US008507723B2

(12) United States Patent
Mousa et al.

(10) Patent No.: US 8,507,723 B2
(45) Date of Patent: *Aug. 13, 2013

(54) POLYCATIONIC COMPOUNDS AND USES THEREOF

(75) Inventors: Shaker Mousa, Wynantskill, NY (US); Dahui Liu, Wynnewood, PA (US)

(73) Assignee: Polymedix, Inc., Radnor, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/529,249

(22) Filed: Jun. 21, 2012

(65) Prior Publication Data

US 2012/0322878 A1  Dec. 20, 2012

Related U.S. Application Data

(63) Continuation of application No. 12/720,734, filed on Mar. 10, 2010, now Pat. No. 8,232,428, which is a continuation of application No. 12/465,995, filed on May 14, 2009, now Pat. No. 7,745,662, which is a continuation of application No. 11/154,962, filed on Jun. 15, 2005, now Pat. No. 7,553,876.

(60) Provisional application No. 60/579,282, filed on Jun. 15, 2004.

(51) Int. Cl.
*C07C 233/05* (2006.01)
*A61K 31/65* (2006.01)

(52) U.S. Cl.
USPC .......................................... 564/153; 514/617

(58) Field of Classification Search
USPC .......................................... 564/153; 514/617
See application file for complete search history.

(56) References Cited

U.S. PATENT DOCUMENTS

| | | | |
|---|---|---|---|
| 5,092,885 A | 3/1992 | Yamada | |
| 5,112,946 A | 5/1992 | Maione | |
| 5,192,744 A | 3/1993 | Bouck | |
| 5,202,352 A | 4/1993 | Okada et al. | |
| 7,553,876 B2 * | 6/2009 | Shaker | 514/617 |
| 7,745,662 B2 | 6/2010 | Mousa et al. | |
| 8,129,566 B2 * | 3/2012 | Mousa et al. | 564/153 |
| 2004/0097401 A1 | 5/2004 | Datta | |
| 2006/0041023 A1 | 2/2006 | Degrado et al. | |

FOREIGN PATENT DOCUMENTS

| | | |
|---|---|---|
| WO | 98/03573 A1 | 1/1998 |
| WO | 02/060488 A1 | 8/2002 |
| WO | 02/100295 | 12/2002 |
| WO | 2004/082634 A1 | 9/2004 |
| WO | 2006/040579 A1 | 4/2006 |
| WO | 2006/093813 A1 | 9/2006 |

OTHER PUBLICATIONS

Gong et al., Creating nanocavities of tunable sizes: Hollow helices, 2002, PNAS 99(18):11583-11588.
Folkman, et al.,; Inhibition of Angiogenesis; Cancer Biology; vol. 3, 1992; pp. 89-96.
Moses, et al.,; Identification of an Inhibitor of Neovascularization From Cartilage; Science, vol. 248, pp. 1408-1410.
Blood, et al.; Tumor Interactions With the Vasculature; Angiogenesis and Tumor Metastasis; Biochimica et Biophysica Acta; 1032 (1990) pp. 89-118; Elsevier Science Publishers B.V. (Biomedical Division).
Cogan, et al., J. Med. Chem., 2003, 46, 5258-5270.
Huff, J. Med. Chem., 1991;vol. 34, No. 8:2305-2314.
National Eye Institute, Congressional Justification of FY 2004,]http://www.nei.nih.gov/news/congressjust/cj2004.asp.
National Cancer Institute, Bevacizumab Combined with Chemotherapy Prolongs Survival for Some Patients with Advanced Lung Cancer, htfp/www.cancer.gov/newscenter/pressreleasea/AvastinLung.
National Cancer Institute, Bevacizumab Combined with Chemotherapy Improves Progression-Free Survival for Patients with Advanced Breast Cancer, http://www.cancer.gov/newscenter/pressreleases/AvastinBreast.
National Cancer Institute, Thalidomide Shows Activity Against. AIDS-Related Kaposi's Sarcoma, http/www.cancer.gov/newscenter/thalidomideks.
National Cancer Institute, Bevacizumab (Avastin) Improves Survival in Metastatic Colorectal Cancer, cancer.gov/clini{altrials/results/bevacizumab-and-colorectal-cancer0601.
National Cancer Institute, Adding Bevacizumab (Avastin) Improves Outcomes in Advanced Colorectal Caricer. http://www.cancer.gov/clinicaltrials/results/bevacizumab-and-coloreGtaf0505.
National Cancer Institute, Molecular Targeted Drug Slows Tumor Growth in Patients with Metastatic Kidney Cancer, http://www.cancer.gov/newscenter/Yang.
National Cancer Institute, Bevacizumab Combined with OxalipiatJn-Based Chemotherapy Prolongs Survival for Previously Treated Patients with Advanced Colorectal Cancer http://www.cancer.gov/newscenter/pressreleases/BevacizumabOxaliplatin.
National Cancer Institute, Bevacizumab (Avastin) for Treatment of Solid Tumors: Questions and Answers, http://www.cancer.gov/cancertopics/factsheet/AvastinFactSheet.
Erwin A. Kruger et al, TNP-470: an angiogenesis inhibitor in clinical development for cancer, Expert Opinion on Investigational Drugs, 2000, pp. 1383-1396,9(6), Ashley Publications Ltd.
Amir Abdollahi et al., Combined Therapy with Direct and Indirect Angiogenesis Inhibition Results in Enhanced Antiangiogenic and antitumor Effects, Cancer Research 63, Dec. 15, 2003, pp. 8890-2298.

(Continued)

*Primary Examiner* — Shailendra Kumar
(74) *Attorney, Agent, or Firm* — Pepper Hamilton LLP

(57) ABSTRACT

Aspects of the present invention relate to compounds and methods useful in modulating angiogenesis and methods of treating or preventing diseases associated with angiogenesis by administering a polycationic compound. The present invention relates to methods of use and compositions for inhibiting angiogenesis-mediated disorders in mammals including animals and humans. Additionally, this invention relates to the combined use of polycations with other anti-angiogenesis agents for the treatment of different angiogenesis-mediated disorders. Additionally, those polycationic compounds can be used with various anti-inflammatory and cytotoxic agents as well as with radio-therapeutic agents in cancer patients to prevent and treat tumor growth and metastasis.

13 Claims, 3 Drawing Sheets

(56) References Cited

OTHER PUBLICATIONS

Evangelos S. Gragoudas et al. Pegaptanibfor Neovascular Age-Related Macular Degneration, The New England Journal of Medicine, Dec. 30, 2004, pp. 2805-2816, 351; 27.

Xinkang Wang et al., Inhibition of Factor Xa Reduces Ischemic Brain Damage After Thromboembokic Stroke in Rats, Stroke, Feb. 2003, pp. 468-474.

Kazimierz Ostrowski et al., Inhibition of Angiogenesis in tie Treatment of Tumors, Archivum Immuhologiae et therapiac Experimentalis, 2001, pp. 27-31,49.

W. R. Gould et al., Recent Advances in the Discovery and Development of Direct Coagulation Factor Xa Inhibitors, Current Pharmaceutical Design, 2003, pp. 2337-2347.9. Bentham Science Publishers Ltd.

Hiroakimatsuno etal., Treatment with Angiogenesis Inhibitor Endostatin: A Novel Therapy in Rheumatoid Arthritis, The Journal of Rheumatology, 2002, pp. 890-895, 29:5.

Marian Ziche et al, Development of New Drugs in Angiogenesis. Current Drug Targets. 2004. pp. 485-493, 5, Bentham Science Publishers Ltd.

Afshin Shafieeetal., Inhibition of Retinal angiogenesis by Peptides Derived from Thrombospondin-i:, Investigative Ophthalmology & Visual Science, Jul. 2000, pp. 2378-2388, vol. 41, No. 8.

Gary W. McCollum et al., Herbimycin A inhibits angiogepic activity in endothelial cells and reduces neovascuiarization in a rat model of retinopathy of prematurity! Experimental Eye Research 78, 2007, pp. 987-995.

Joel R. Huff, HIV Protease: A Novel Chemotherapeutic Target for AIDS, Journal of Medicinal Chemistry, Aug. 1991, pp. 2305-2314, vol. 34. No. 6.

M. Hess et al., Terminology of Polymers Containing Ionizable or Ionic Groups and of Polymers Containing Ions, International Union of Pure and Applied Chemistry, Dec. 23, 2004, pp. 1-12.

Dings, R. P., et al., Discovery and development of anti-angiogenic peptides: A structural link, Angiogenesis. 2003;6 (2):83-91.

Liu, D., et al., Nontoxic membrane-active antimicrobial arylamide oligomers, Angew Chem Int Ed Engl. Feb. 20, 2004;43(9):1158-62.

Carter, et al., Chemotherapy of Cancer, second edition, John Wiley & Sons, N.Y., N.Y., 1981, pp. 362-365.

Notice of Allowance for related U.S. Appl. No. 11/154,962 dated Jan. 2, 2009.

Non-final office action for related U.S. Appl. No. 11/154,962 dated Mar. 10, 2008.

Non-final office action for related U.S. Appl. No. 11/154,962 dated Aug. 24, 2007.

Final office action for related U.S. Appl. No. 11/154,962 dated Feb. 1, 2007.

Non-final office action for related U.S. Appl. No. 11/154,962 dated Aug. 16, 2006.

Notice of Allowance for related U.S. Appl. No. 12/465,995 dated Feb. 18, 2010.

Non-final office action for related U.S. Appl. No. 12/465,995 dated Oct. 1, 2009.

Ex Parte Quayle Action for related U.S. Appl. No. 12/720,734 dated May 31, 2011.

Non-final office action for related U.S. Appl. No. 12/720,734 dated Jan. 5, 2011.

Choi, S., et al., The design and evaluation of heparin-binding foldamers, Angew Chem Int Ed Engl. Oct. 21, 2005;44 (41):6685-9.

Non-final office action for related U.S. Appl. No. 12/720,734 dated Sep. 9, 2011.

Final office action for related U.S. Appl. No. 12/720,734 dated Jan. 17, 2012.

Notice of Allowance for related U.S. Appl. No. 12/720,734 dated Mar. 21, 2012.

Non-final office action for related U.S. Appl. No. 12/971,006 dated Jul. 18, 2011.

Notice of Allowance for related U.S. Appl. No. 12/971,006 dated Oct. 27, 2011.

* cited by examiner

US 8,507,723 B2

POLYCATIONIC COMPOUNDS AND USES THEREOF

REFERENCE TO RELATED APPLICATIONS

This application claims priority under 35 U.S.C. §120 as a continuation of U.S. application Ser. No. 12/720, 734, filed Mar. 10, 2010, now U.S. Pat. No. 8,232,428, which is a continuation of U.S. application Ser. No. 12/465,995, filed May 14, 2009, now U.S. Pat. No. 7,745,662, which is a continuation of U.S. application Ser. No. 11/154,962 filed Jun. 15, 2005, now U.S. Pat. No. 7,553,876, which claims priority under 35 U.S.C. §119(e) to U.S. Provisional Application Ser. No. 60/579,282 filed on Jun. 15, 2004, each of which is incorporated herein by reference in its entirety.

BACKGROUND OF THE INVENTION

Angiogenesis is the development of new blood vessels from preexisting blood vessels Physiologically, angiogenesis ensures proper development of mature organisms, prepares the womb for egg implantation, and plays a key role in wound healing, fracture repair, and the establishment and maintenance of pregnancy. Angiogenesis is also associated with pathological conditions associated with a number of disease states such as cancer, inflammation, and ocular diseases.

Angiogenesis or "neovascularization" is a multi-step process controlled by the balance of pro- and anti-angiogenic factors. The latter stages of this process involve proliferation and organization of endothelial cells (EC) into tube-like structures. Growth factors such as fibroblast growth factor 2 (FGF2) and vascular endothelial growth factor (VEGF) are thought to be key players in promoting endothelial cell growth and differentiation. The endothelial cell is the pivotal component of the angiogenic process and responds to many cytokines through its cell surface receptors and intracellular signaling mechanisms.

Control of angiogenesis is a complex process involving local release of vascular growth factors, extracellular matrix adhesion molecules, and metabolic factors. Mechanical forces within blood vessels may also play a role. The principal classes of endogenous growth factors implicated in new blood vessel growth are the fibroblast growth factor (FGF) family and vascular endothelial growth factor (VEGF). The mitogen-activated protein kinase (MAPK; ERK 1/2) signal transduction cascade is involved both in VEGF gene expression and in control of proliferation of vascular endothelial cells.

Many diseases and undesirable conditions could be prevented or alleviated if it were possible to stop the growth and extension of capillary blood vessels under some conditions, at certain times, or in particular tissues. Angiogenesis-dependent diseases that can be treated by the invention disclosed herein are those conditions/diseases which require or induce vascular growth. On the other hand, promotion of angiogenesis is desirable in situations where vascularization is to be established or extended, such as, but not limited to, stroke, heart disease, ulcers, scleroderma and infertility.

It has been proposed that inhibition of angiogenesis would be a useful therapy for restricting the unregulated growth of blood vessels, for example, in tumor growth. Inhibition of angiogenesis can be achieved by inhibiting endothelial cell response to angiogenic stimuli as suggested by Folkman et al., *Cancer Biology* 3:89-96 (1992), where examples of endothelial cell response inhibitors such as angiostatic steroids, fungally derived products such as fumagilin, platelet factor 4, thrombospondin, alpha-interferon, vitamin D analogs, and D-penicillamine are described. For additional proposed inhibitors of angiogenesis, see Blood et al., *Bioch. Biophys. Acta* 1032:89-118 (1990), Moses et al., *Science* 248:1408-1410 (1990), and U.S. Pat. Nos. 5,092,885, 5,112, 946, 5,192,744, and 5,202,352.

Inhibiting an undesired angiogenic processes may provide a therapeutic treatment and/or preventive against inappropriate or undesired angiogenesis. Conversely, promoting an angiogenic process may provide a therapeutic treatment for those diseases states that would benefit from angiogenesis. Aspects of the invention disclosed herein provide amphiphilic compounds, such as polycationic compounds, for their anti-angiogenic properties. The ability to inhibit angiogenesis may provide an effective therapeutic tool for modulating angiogenic diseases and/or conditions.

SUMMARY OF THE INVENTION

An aspect of the present invention relates to polycationic compounds and compositions containing polycationic compounds useful in modulating angiogenesis.
Polycationic Another aspect of the present invention relates to a method of modulating angiogenesis in an animal or human in need thereof comprising administering to said animal a therapeutically effective amount of a polycationic compound.

A further aspect of the present invention also relates to a method of treating or preventing a disease or disorder in an animal or human in need thereof, comprising administering to said animal a therapeutically effective amount of an polycationic compound.

DESCRIPTION OF THE INVENTION

Figure 1:
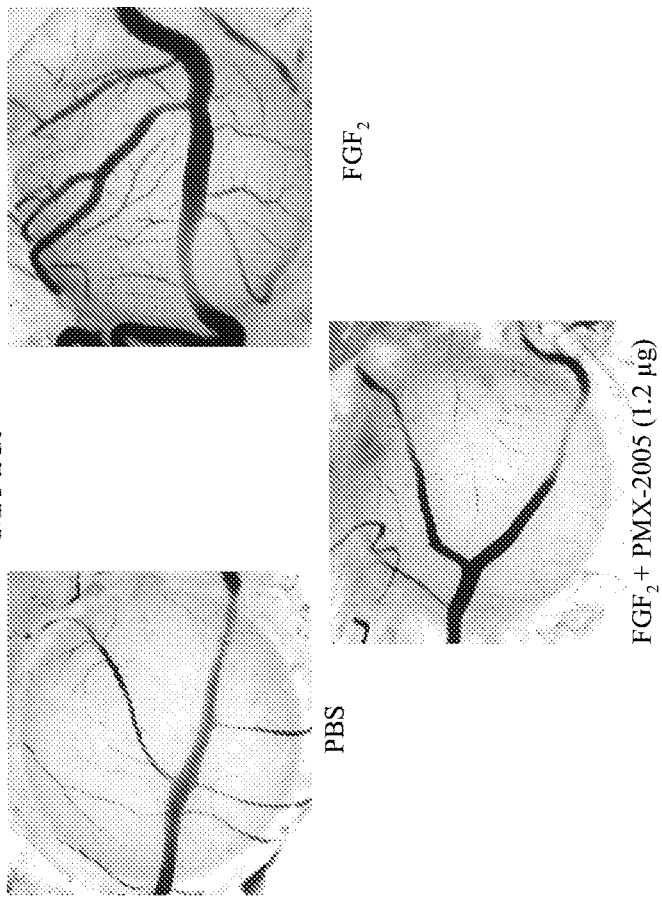
FIG. 1 depicts the effect of polycationic compounds in the CAM model of angiogenesis.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

The terms "angiogenesis" or "neovascularization" refer to the generation of new blood supply, e.g., blood capillaries, vessels, and veins, from existing blood vessel tissue (e.g., vasculature). The process of angiogenesis can involve a number of tissue cell types including, for example, endothelial cells which form a single cell layer lining of all blood vessels and are involved with regulating exchanges between the bloodstream and the surrounding tissues. New blood vessels (angiogenesis) can develop from the walls of existing small vessels by the outgrowth of endothelial cells. Angiogenesis is also involved in tumor growth as it provides tumors with blood supply necessary for tumor cell survival and proliferation (growth).

The terms "patient" and "subject" mean all animals including humans. Examples of patients or subjects include humans, cows, dogs, cats, goats, sheep, and pigs.

A "therapeutically effective amount" in reference to pharmaceutical compositions is an amount sufficient to decrease or prevent the symptoms associated with a medical condition or infirmity, to normalize body functions in disease or disorders that result in impairment of specific bodily functions, or to provide improvement in one or more of the clinically measured parameters of the disease. As related to the present application, a therapeutically effective amount of a polycationic compound is an amount sufficient to decrease or inhibit angiogenesis.

Aspects of the present invention relate to methods of modulating angiogenesis in an animal in need thereof comprising administering to the animal a therapeutically effective amount of a polycationic compound. Aspects of the present invention also relate to methods of treating or preventing a disease or disorder in an animal in need thereof, comprising administering to the animal a therapeutically effective amount of a polycationic compound.

Generally, the polycationic compounds preferably exhibit a rigid or semi-rigid backbone, such that the structure is torsionally-constrained, that displays positively-charged sidegroups on one face of the backbone. The positively charged sidegroups are optimally distributed along the length of the backbone and optimally separated from the backbone by a carbon spacer that may optionally contain one or more heteroatoms. Torsional freedom along the backbone may be stabilized by intramolecular hydrogen bonding, steric constraints or cyclization. While preferred formulas of various polycationic compounds, such as arylamides, hydrazides, calixrenes and salicylamides, are described, other suitable sidegroups that may be used to stabilize the positive charge include, for example, (A-G):

Me₂N—    A

MeHN—    B

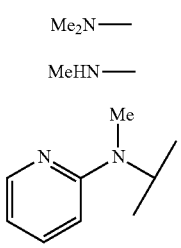    C

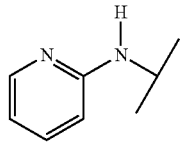    D

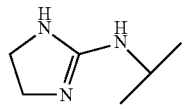    E

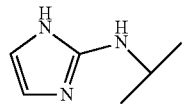    F

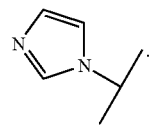    G

Other amines that may be used include, for example, piperidine, 4-aminopyridine, morpholine, and aminothiazole. Optionally, the basicity of an amino group may be modulated by incorporating 1 or 2 fluorines on one of the methylene groups in the chain. Other center ring substituents that may also be used to rigidify (reduce torsional freedom) of the backbone include, for example, (H-K):

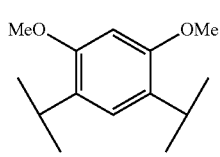    H

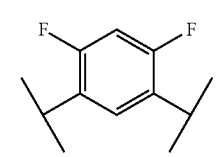    I

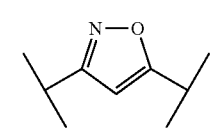    J

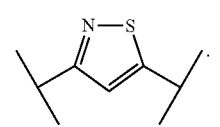    K

In one embodiment of the invention, the polycationic compound is an arylamide oligomer compound of the formula:

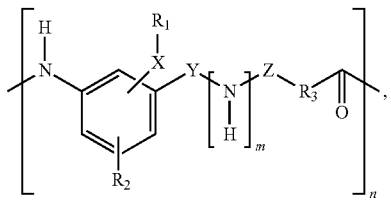

wherein
X is O or S;
$R_1$ is $C_1$-$C_9$ straight or branched chain alkyl, wherein $R_1$ is optionally substituted with one or more —$NH_2$ or

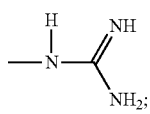

Y is a bond or

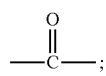

Z is a bond or

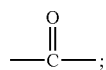

$R_2$ is hydrogen or $C_1$-$C_9$ straight or branched chain alkyl; wherein said $R_2$ is optionally substituted with one or more —$NH_2$ or

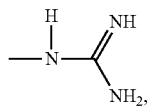

or $R_2$ is —X—$R_1$;
$R_3$ is

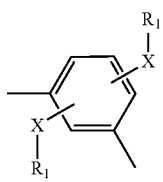

or methylene,
wherein said methylene is substituted with $C_1$-$C_9$ straight or branched chain alkyl, wherein said $C_1$-$C_9$ straight or branched chain alkyl is optionally substituted with one or more —$NH_2$ or

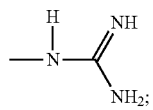

n is 2-10; and
m is 1 or 2.

In another embodiment of the invention, the arylamide oligomer compound is a compound of the formula:

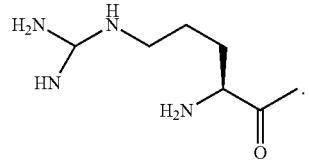

wherein $R_1$ is

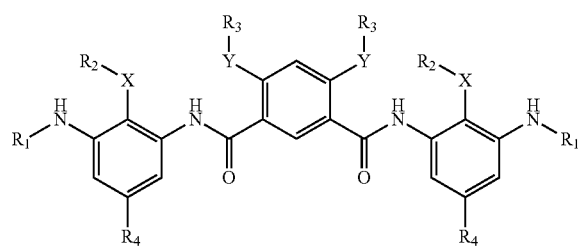

In a preferred embodiment, the compound is an arylamide of the formula:

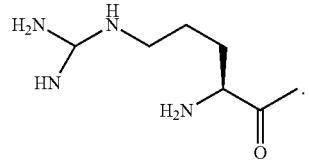

X is O or S;
Y is O or S;
$R_1$ is H or —C(=O)-A, A $C_1$ to $C_9$ straight or branched alkyl, where A is optionally substituted with one or more —$NH_2$, —$N(CH_3)_2$ or

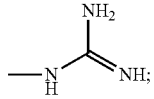

$R_2$ is $C_1$ to $C_9$ straight or branched alkyl, where $R_2$ is optionally substituted with one or more —$NH_2$, —$N(CH_3)_2$ or

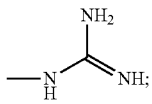

$R_3$ is $C_1$ to $C_9$ straight or branched alkyl, where $R_3$ is optionally substituted with one or more —$NH_2$, —$N(CH_3)_2$ or

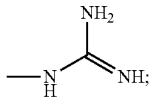

$R_4$ is H, —B or —C(=O)—O—B, where B is $C_1$ to $C_9$ straight or branched alkyl.

In another embodiment, the polycationic compound is a hydrazide of the formula:

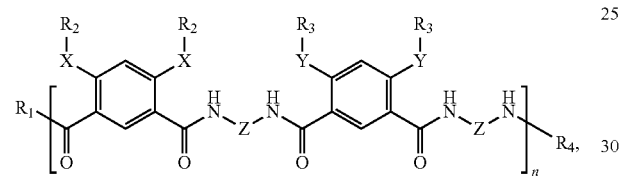

wherein
n=1 to 10;
X is O or S;
Y is O or S;
Z is a bond, $C_1$ to $C_9$ straight or branched alkyl, or a 1,4-cyclohexyl
$R_1$ is $NH_2$ or NH-A, where A is $C_1$ to $C_9$ straight or branched alkyl, where A is optionally substituted with —$NH_2$, —$N(CH_3)_2$ or

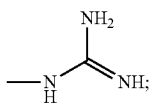

$R_2$ is $C_1$ to $C_9$ straight or branched alkyl, where $R_2$ is optionally substituted with one or more —$NH_2$, —$N(CH_3)_2$ or

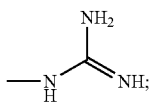

$R_3$ is $C_1$ to $C_9$ straight or branched alkyl, where $R_3$ is optionally substituted with one or more —$NH_2$, —$N(CH_3)_2$ or

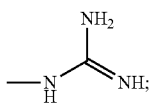

$R_4$ is H or

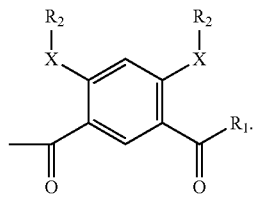

In another embodiment of the invention, the polycationic compound is a calixrene of the formula:

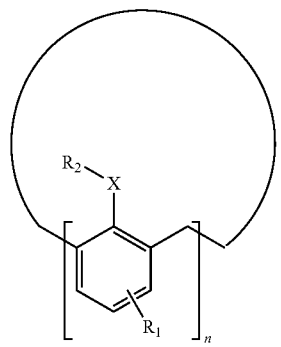

wherein
n=2-8, more preferably 4-8;
X is a bond, O or —O—$CH_2$—C(=O)—O—,
$R_1$ is –A or —O-A, where A is $C_1$ to $C_9$ straight or branched alkyl;
$R_2$ is $C_1$ to $C_9$ straight or branched alkyl, where $R_2$ is optionally substituted with one or more —$NH_2$, —$N(CH_3)_2$ or

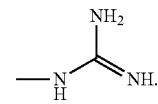

In another embodiment of the invention, the polycationic compound is a salicylamide of the formula:

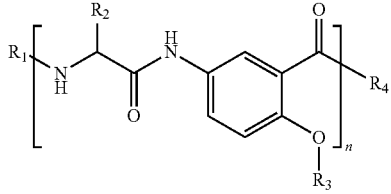

n is 2 to 10;
$R_1$ is H or

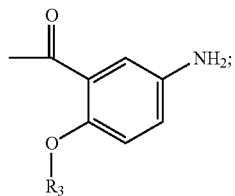

$R_2$ is $C_1$ to $C_9$ straight or branched alkyl, where $R_2$ is optionally substituted with one or more —$NH_2$, —$N(CH_3)_2$ or

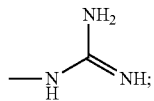

$R_3$ is $C_1$ to $C_9$ straight or branched alkyl, where $R_2$ is optionally substituted with one or more —$NH_2$, —$N(CH_3)_2$ or

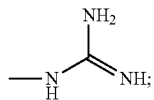

$R_4$ is OH, $NH_2$ or

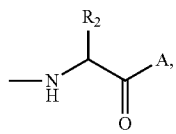

where A is OH or $NH_2$.

In a further embodiment, the polycationic compound is selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, Compound 27, Compound 28, Compound 29, Compound 30, Compound 31, Compound 32, Compound 33, Compound 34, Compound 35, Compound 26, Compound 37, Compound 38, Compound 39, Compound 40, Compound 41, Compound 42, Compound 43, Compound 44, Compound 45, Compound 46, Compound 47, Compound 48, Compound 49, Compound 50, Compound 51, Compound 52, Compound 53, Compound 54 and Compound 55, as depicted below in Table 1.

While Compound 1 and Compound 2 comprise the same arylamide structure, Compound 1 and 2 are synthesized under different conditions and exhibit different purities. During polymerization, DCM (dichloromethane) was used as a solvent for Compound 2 and NMP (1-methyl-2-pyrrolidinone) was used for Compound 1. Polymerization is less efficient in NMP, therefore Compound 1 is n=2-10 and n=10 for Compound 2.

TABLE 1

Polycationic Compounds.

| Compound | Structure |
|---|---|
| Compound 1 | 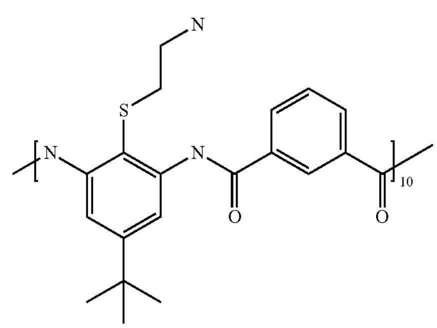 |
| Compound 2 | 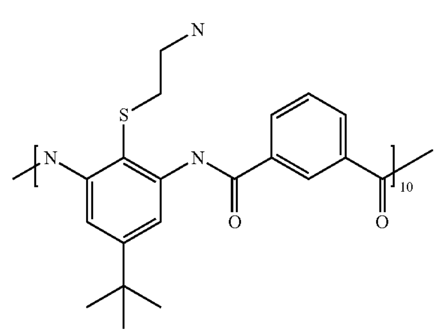 |

TABLE 1-continued

Polycationic Compounds.

| Compound | Structure |
| --- | --- |
| Compound 3 | 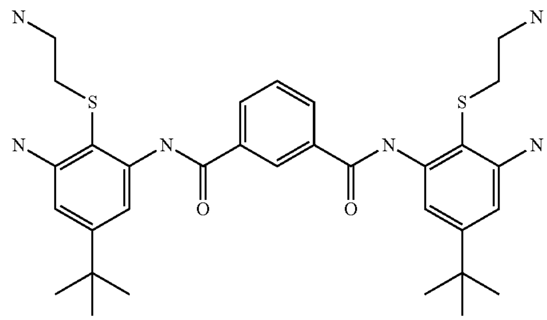 [SMILES: CC(C)(C)c1cc(N)c(SCCN)c(NC(=O)c2cccc(C(=O)Nc3cc(C(C)(C)C)cc(N)c3SCCN)c2)c1] |
| Compound 4 | 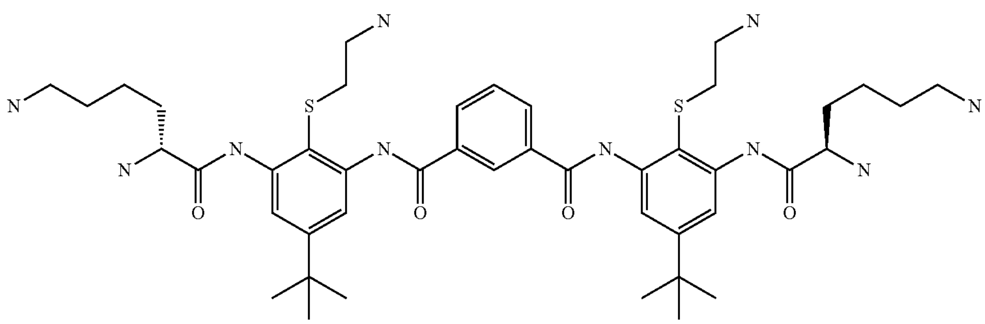 [SMILES: CC(C)(C)c1cc(NC(=O)c2cccc(C(=O)Nc3cc(C(C)(C)C)cc(NC(=O)[C@H](N)CCCCN)c3SCCN)c2)c(SCCN)c(NC(=O)[C@H](N)CCCCN)c1] |
| Compound 5 | 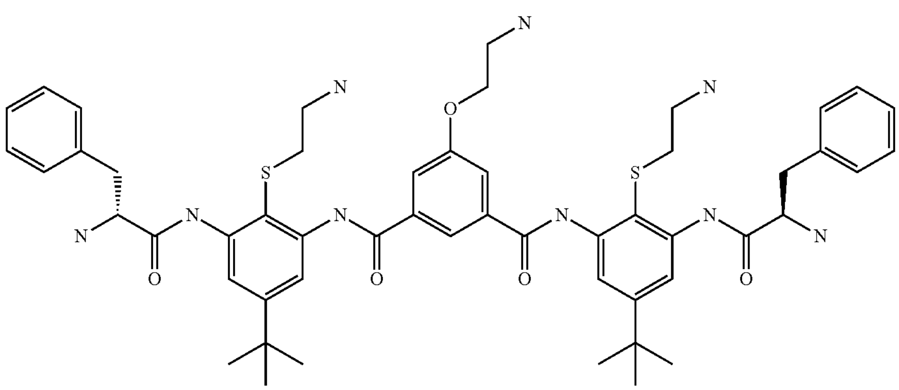 [SMILES: CC(C)(C)c1cc(NC(=O)c2cc(OCCN)cc(C(=O)Nc3cc(C(C)(C)C)cc(NC(=O)[C@H](N)Cc4ccccc4)c3SCCN)c2)c(SCCN)c(NC(=O)[C@H](N)Cc2ccccc2)c1] |
| Compound 6 | 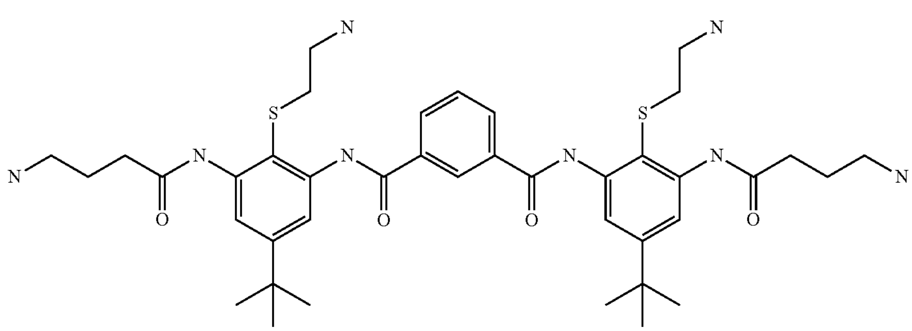 [SMILES: CC(C)(C)c1cc(NC(=O)CCCN)c(SCCN)c(NC(=O)c2cccc(C(=O)Nc3cc(C(C)(C)C)cc(NC(=O)CCCN)c3SCCN)c2)c1] |

TABLE 1-continued

Polycationic Compounds.

| Compound | Structure |
|---|---|
| Compound 7 | 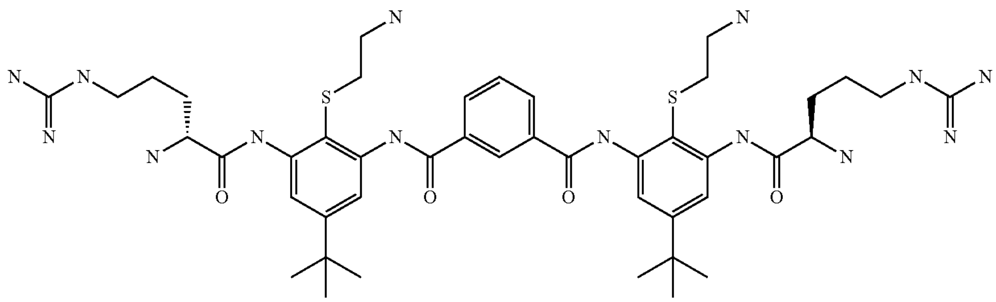 [SMILES: CC(C)(C)c1cc(NC(=O)c2cccc(C(=O)Nc3cc(C(C)(C)C)cc(NC(=O)[C@H](N)CCCNC(=N)N)c3SCCN)c2)c(SCCN)c(NC(=O)[C@H](N)CCCNC(=N)N)c1] |
| Compound 8 | 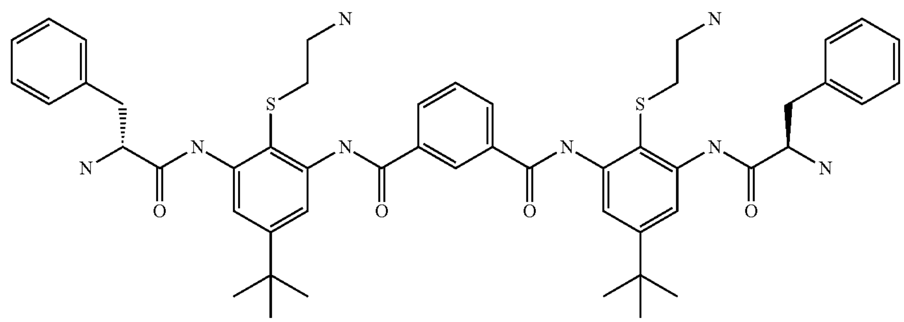 [SMILES: CC(C)(C)c1cc(NC(=O)c2cccc(C(=O)Nc3cc(C(C)(C)C)cc(NC(=O)[C@H](N)Cc4ccccc4)c3SCCN)c2)c(SCCN)c(NC(=O)[C@H](N)Cc2ccccc2)c1] |
| Compound 9 | 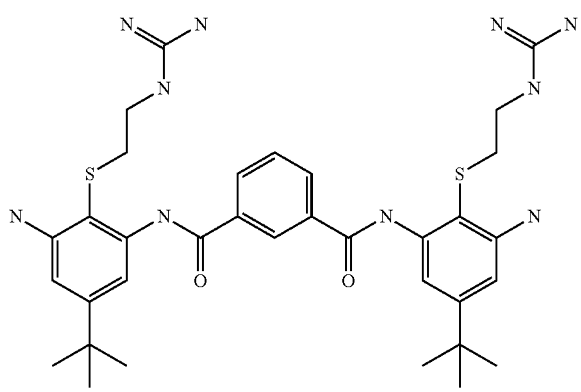 [SMILES: CC(C)(C)c1cc(N)c(SCCNC(=N)N)c(NC(=O)c2cccc(C(=O)Nc3cc(C(C)(C)C)cc(N)c3SCCNC(=N)N)c2)c1] |
| Compound 10 | 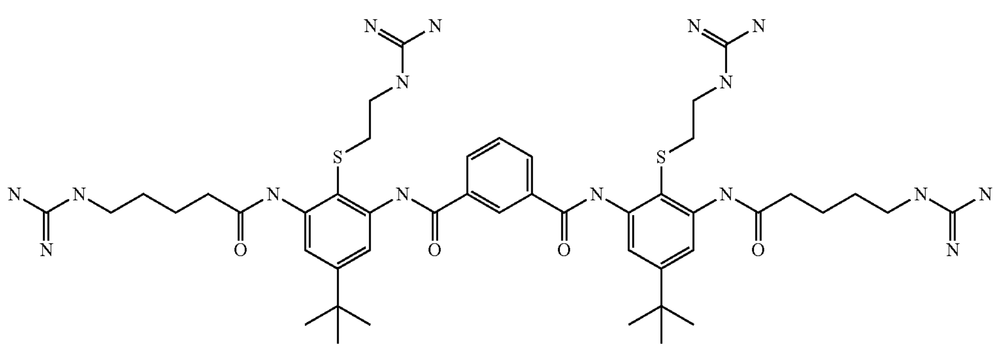 [SMILES: CC(C)(C)c1cc(NC(=O)CCCCNC(=N)N)c(SCCNC(=N)N)c(NC(=O)c2cccc(C(=O)Nc3cc(C(C)(C)C)cc(NC(=O)CCCCNC(=N)N)c3SCCNC(=N)N)c2)c1] |

TABLE 1-continued

Polycationic Compounds.

| Compound | Structure |
|---|---|
| Compound 11 | 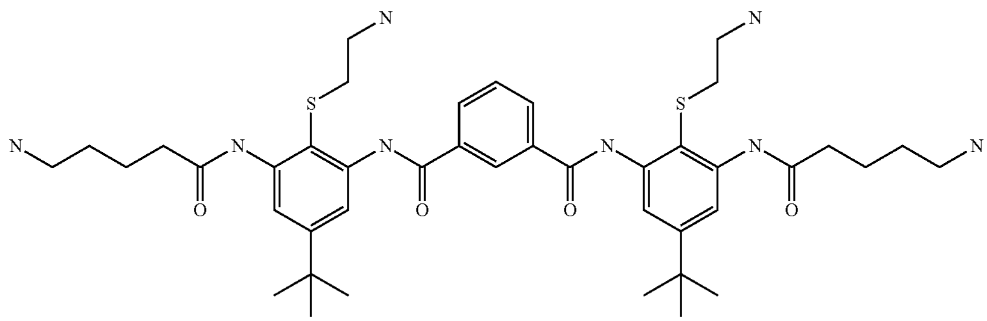 [SMILES: CC(C)(C)c1cc(NC(=O)CCCCN)c(SCCN)c(NC(=O)c2cccc(C(=O)Nc3cc(C(C)(C)C)cc(NC(=O)CCCCN)c3SCCN)c2)c1] |
| Compound 12 | 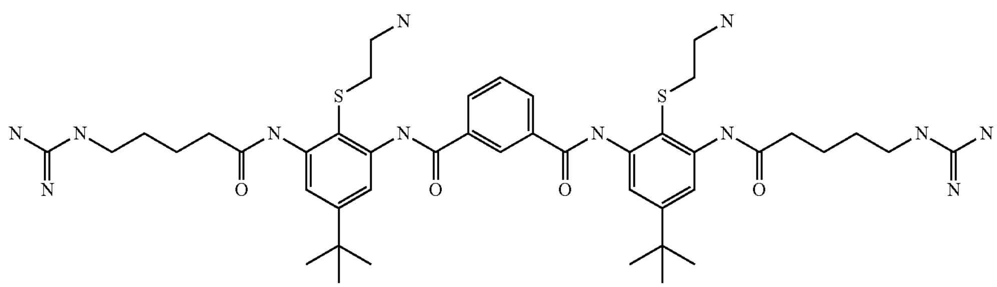 [SMILES: CC(C)(C)c1cc(NC(=O)CCCCNC(=N)N)c(SCCN)c(NC(=O)c2cccc(C(=O)Nc3cc(C(C)(C)C)cc(NC(=O)CCCCNC(=N)N)c3SCCN)c2)c1] |
| Compound 13 | 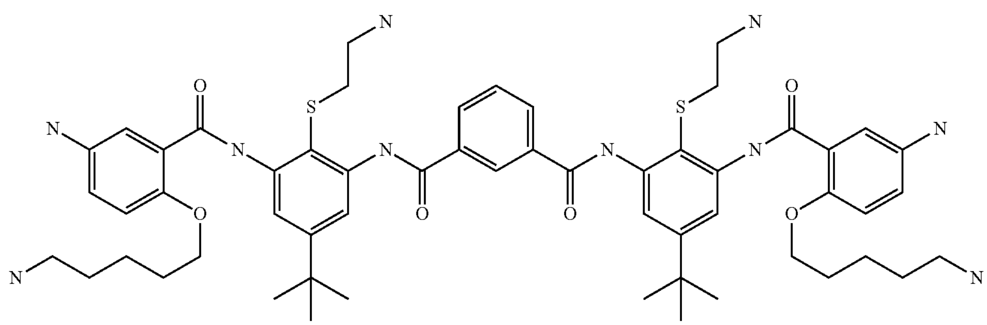 [SMILES: CC(C)(C)c1cc(NC(=O)c2cccc(C(=O)Nc3cc(C(C)(C)C)cc(NC(=O)c4cc(N)ccc4OCCCCCN)c3SCCN)c2)c(SCCN)c(NC(=O)c2cc(N)ccc2OCCCCCN)c1] |
| Compound 14 | 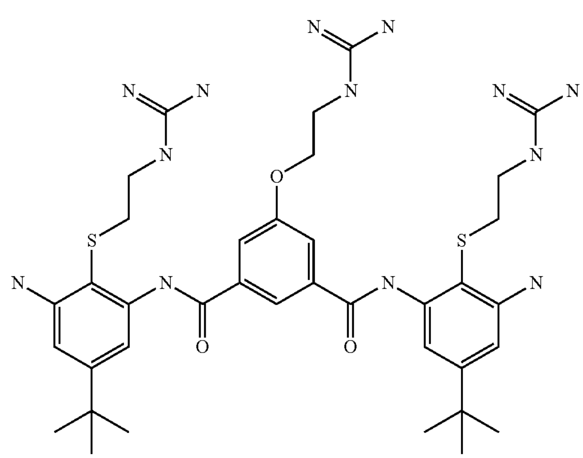 [SMILES: CC(C)(C)c1cc(N)c(SCCNC(=N)N)c(NC(=O)c2cc(OCCNC(=N)N)cc(C(=O)Nc3cc(C(C)(C)C)cc(N)c3SCCNC(=N)N)c2)c1] |

TABLE 1-continued

Polycationic Compounds.

| Compound | Structure |
|---|---|
| Compound 15 | 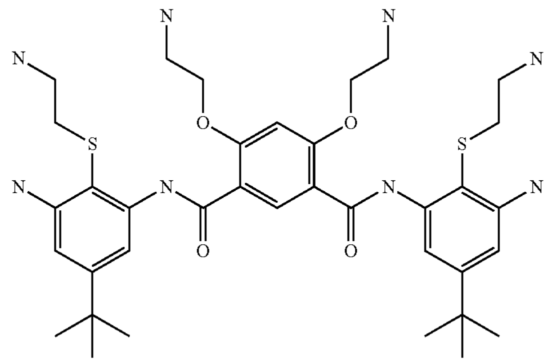 [SMILES: CC(C)(C)c1cc(N)c(SCCN)c(NC(=O)c2cc(C(=O)Nc3cc(C(C)(C)C)cc(N)c3SCCN)c(OCCN)cc2OCCN)c1] |
| Compound 16 | 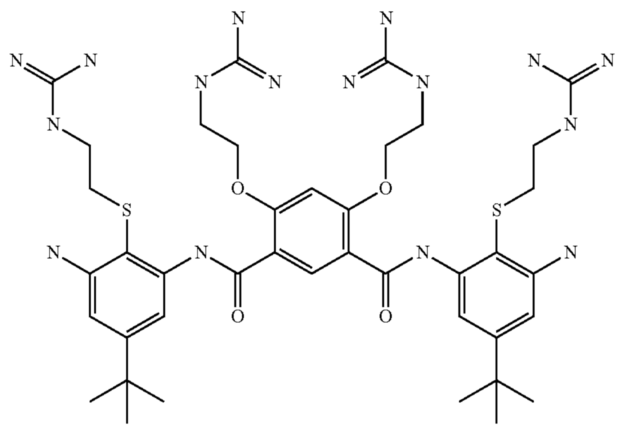 [SMILES: CC(C)(C)c1cc(N)c(SCCNC(=N)N)c(NC(=O)c2cc(C(=O)Nc3cc(C(C)(C)C)cc(N)c3SCCNC(=N)N)c(OCCNC(=N)N)cc2OCCNC(=N)N)c1] |
| Compound 17 | 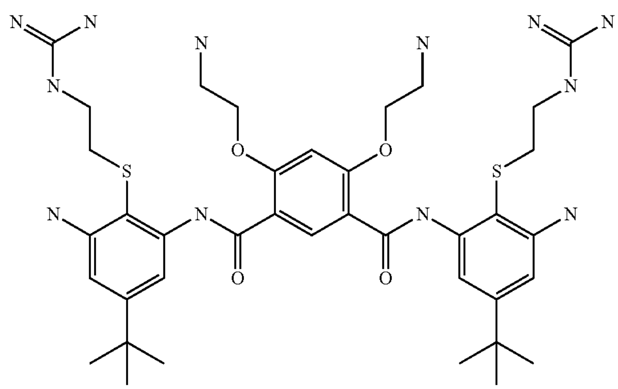 [SMILES: CC(C)(C)c1cc(N)c(SCCNC(=N)N)c(NC(=O)c2cc(C(=O)Nc3cc(C(C)(C)C)cc(N)c3SCCNC(=N)N)c(OCCN)cc2OCCN)c1] |
| Compound 18 | 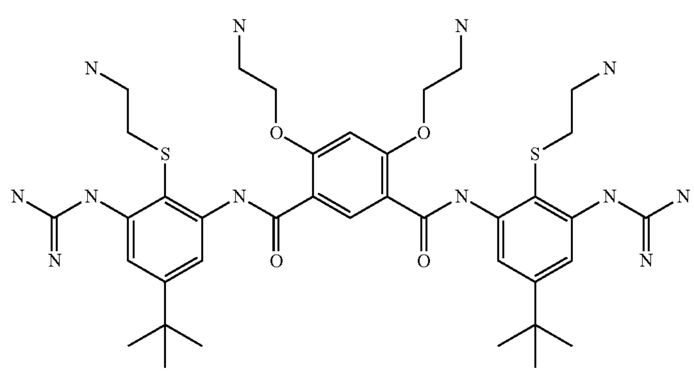 [SMILES: CC(C)(C)c1cc(NC(=N)N)c(SCCN)c(NC(=O)c2cc(C(=O)Nc3cc(C(C)(C)C)cc(NC(=N)N)c3SCCN)c(OCCN)cc2OCCN)c1] |

TABLE 1-continued

Polycationic Compounds.

| Compound | Structure |
|---|---|
| Compound 19 | (structure) |
| Compound 20 | (structure) |
| Compound 21 | (structure) |

TABLE 1-continued

Polycationic Compounds.

| Compound | Structure |
|---|---|
| Compound 22 | 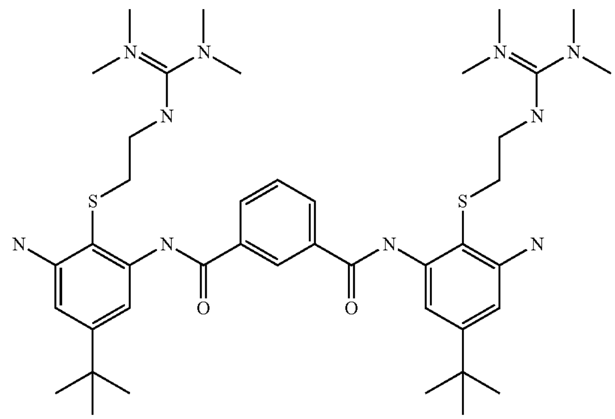 |
| Compound 23 | 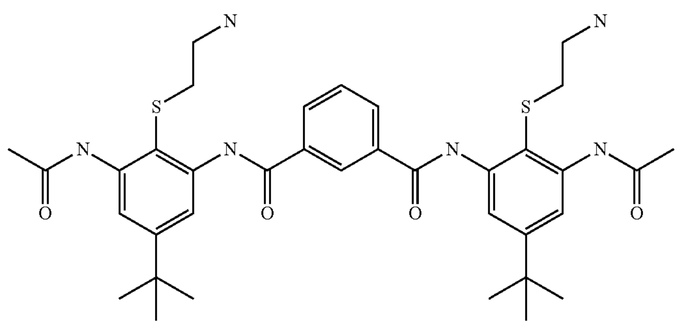 [SMILES: CC(=O)Nc1cc(C(C)(C)C)cc(NC(=O)c2cccc(C(=O)Nc3cc(C(C)(C)C)cc(NC(C)=O)c3SCCN)c2)c1SCCN] |
| Compound 24 | 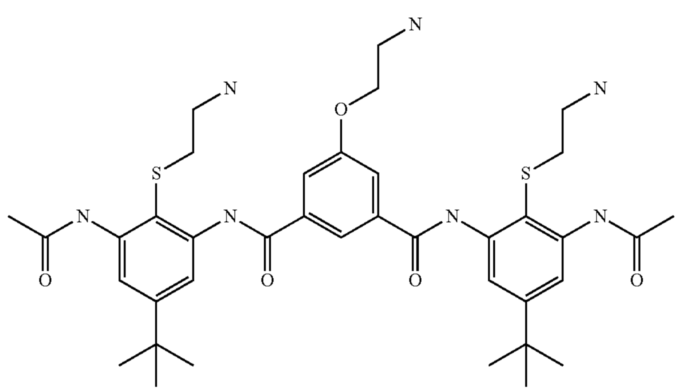 [SMILES: CC(=O)Nc1cc(C(C)(C)C)cc(NC(=O)c2cc(OCCN)cc(C(=O)Nc3cc(C(C)(C)C)cc(NC(C)=O)c3SCCN)c2)c1SCCN] |
| Compound 25 | 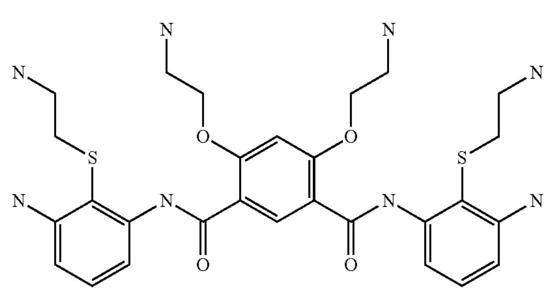 [SMILES: NCCOc1cc(OCCN)c(C(=O)Nc2cccc(N)c2SCCN)cc1C(=O)Nc1cccc(N)c1SCCN] |

TABLE 1-continued

Polycationic Compounds.

| Compound | Structure |
| --- | --- |
| Compound 26 | 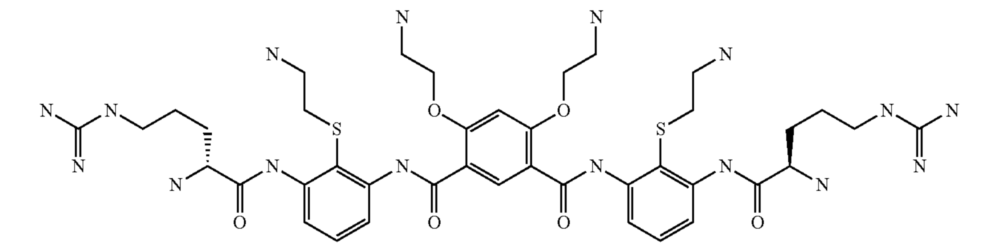 [SMILES: N=C(N)NCCC[C@@H](N)C(=O)Nc1cccc(NC(=O)c2cc(C(=O)Nc3cccc(NC(=O)[C@H](N)CCCNC(=N)N)c3SCCN)c(OCCN)cc2OCCN)c1SCCN] |
| Compound 27 | 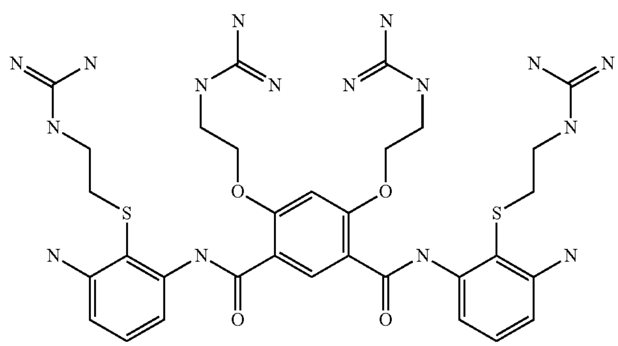 [SMILES: N=C(N)NCCOc1cc(OCCNC(=N)N)c(C(=O)Nc2cccc(N)c2SCCNC(=N)N)cc1C(=O)Nc1cccc(N)c1SCCNC(=N)N] |
| Compound 28 | 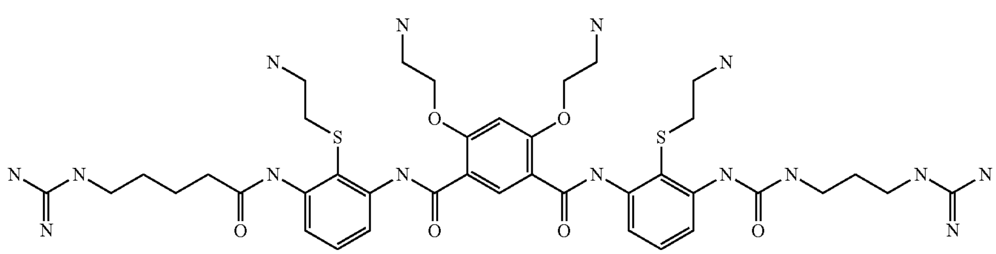 [SMILES: N=C(N)NCCCCC(=O)Nc1cccc(NC(=O)c2cc(C(=O)Nc3cccc(NC(=O)NCCCNC(=N)N)c3SCCN)c(OCCN)cc2OCCN)c1SCCN] |
| Compound 29 | 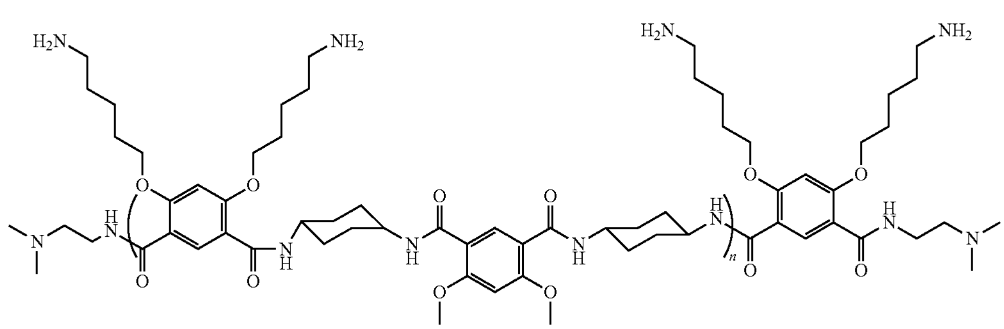 |

TABLE 1-continued

Polycationic Compounds.

| Compound | Structure |
| --- | --- |
| Compound 30 | 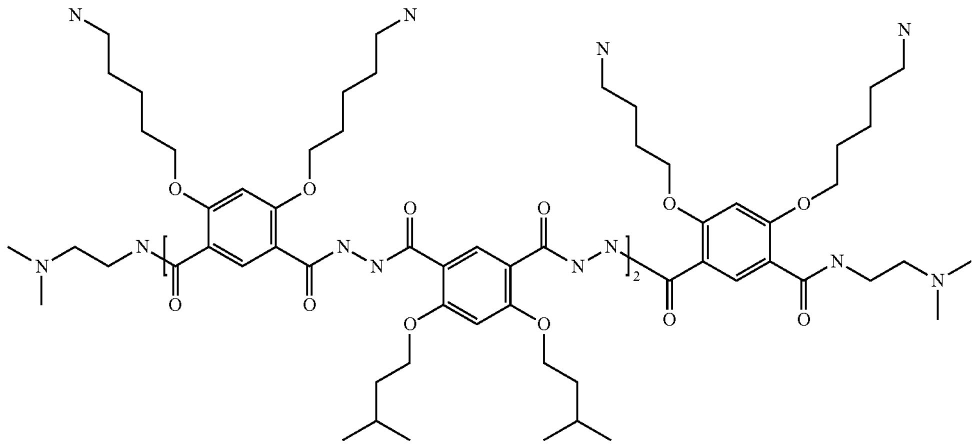 |
| Compound 31 | 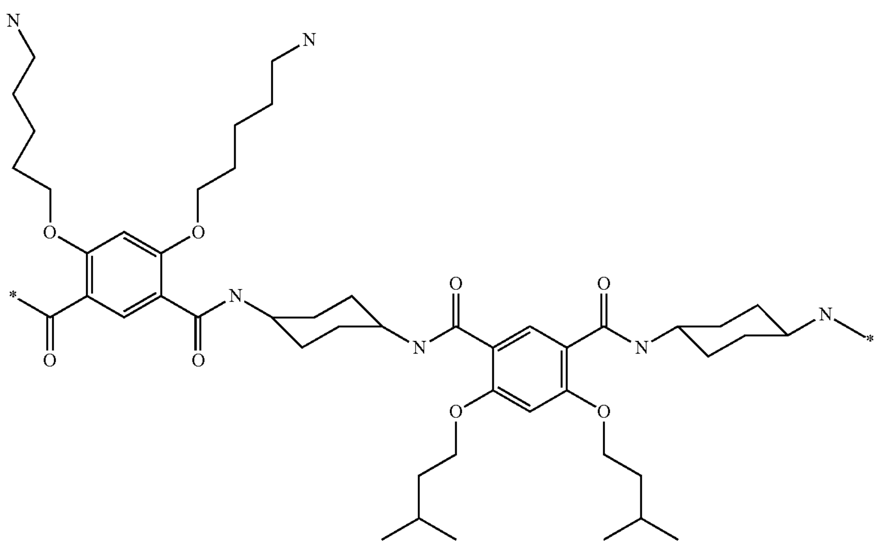 |
| Compound 32 | 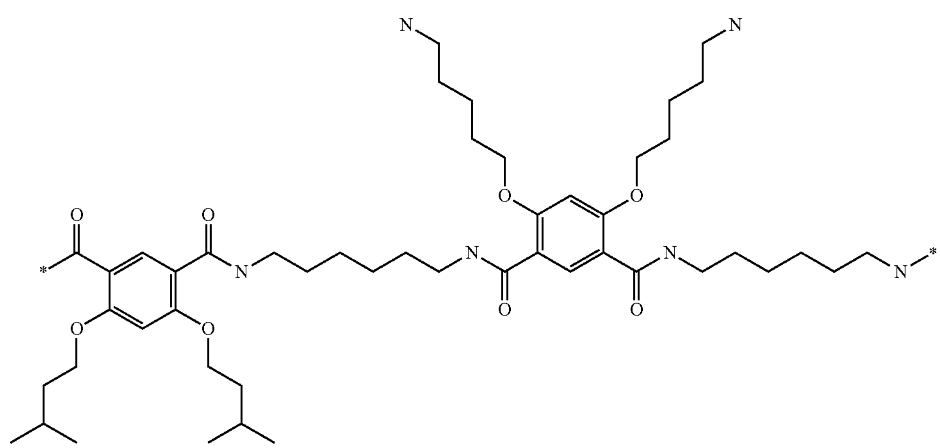 |

TABLE 1-continued

Polycationic Compounds.

| Compound | Structure |
|---|---|
| Compound 33 | 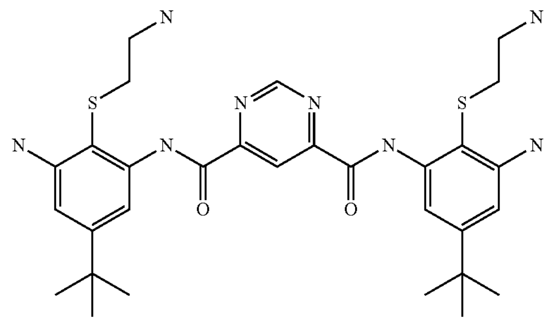 [SMILES: CC(C)(C)c1cc(N)c(SCCN)c(NC(=O)c2cc(C(=O)Nc3cc(C(C)(C)C)cc(N)c3SCCN)ncn2)c1] |
| Compound 34 | 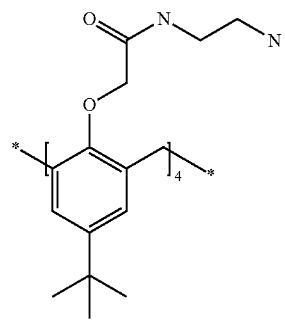 |
| Compound 35 | 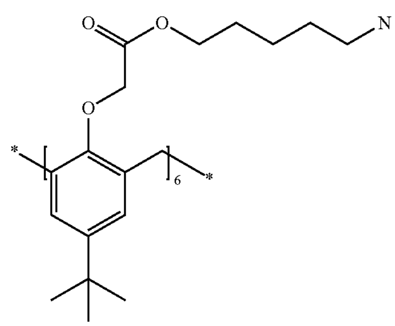 |
| Compound 36 | 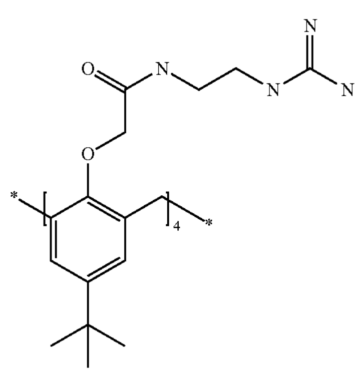 |

TABLE 1-continued

Polycationic Compounds.

| Compound | Structure |
| --- | --- |
| Compound 37 | (structure image) |
| Compound 38 | (structure image) |
| Compound 39 | (structure image) |
| Compound 40 | (structure image) |

TABLE 1-continued

Polycationic Compounds.

| Compound | Structure |
|---|---|
| Compound 41 | 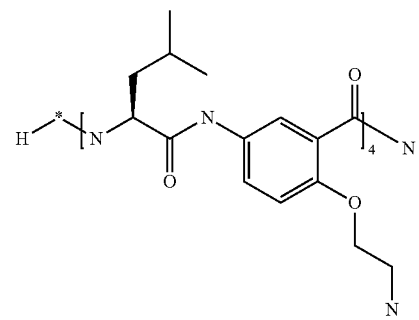 |
| Compound 42 | 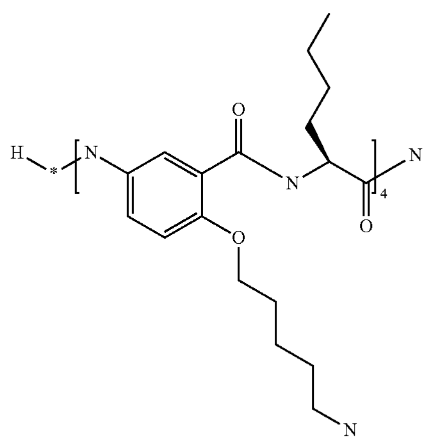 |
| Compound 43 | 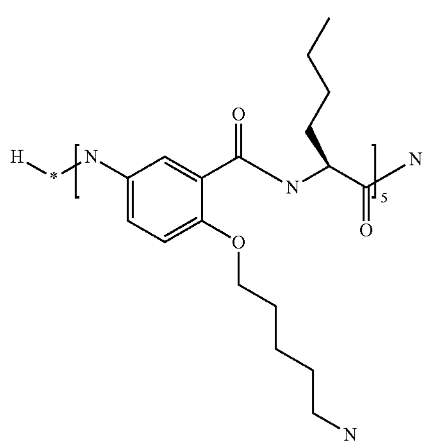 |

TABLE 1-continued

Polycationic Compounds.

| Compound | Structure |
|---|---|
| Compound 44 | 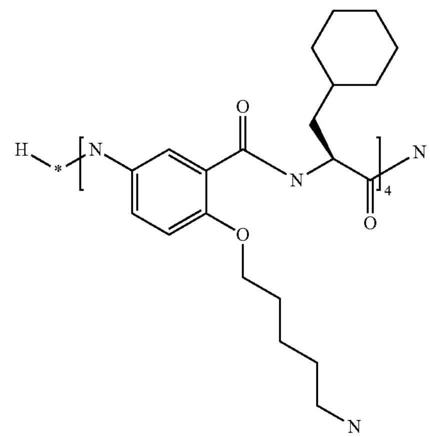 |
| Compound 45 | 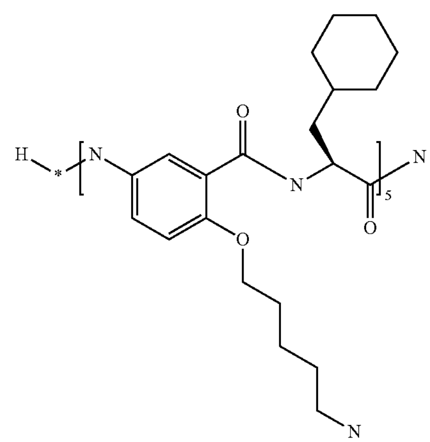 |
| Compound 46 | 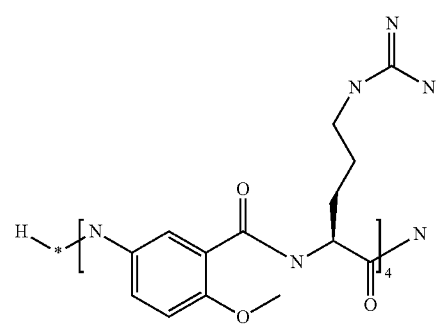 |
| Compound 47 | 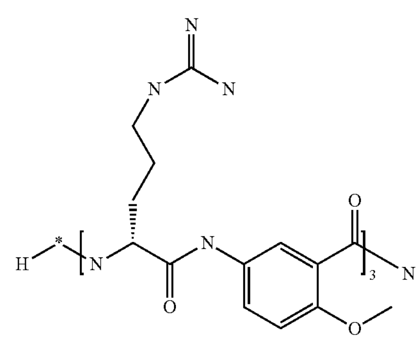 |

TABLE 1-continued

Polycationic Compounds.

| Compound | Structure |
|---|---|
| Compound 48 | 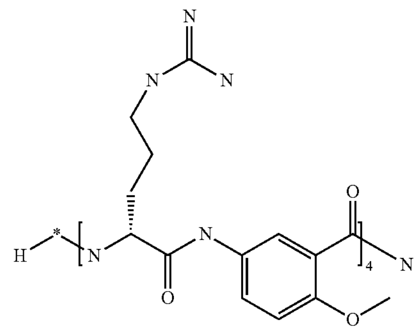 |
| Compound 49 | 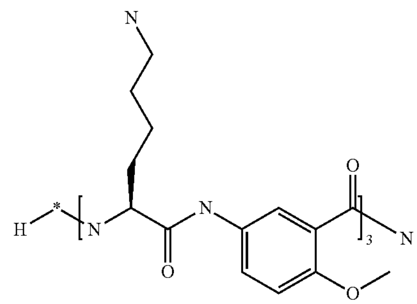 |
| Compound 50 | 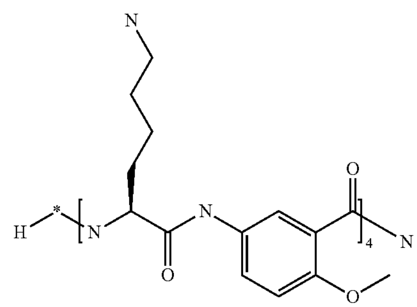 |
| Compound 51 | 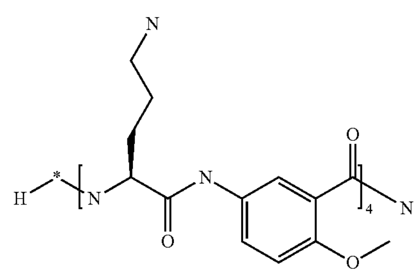 |
| Compound 52 | 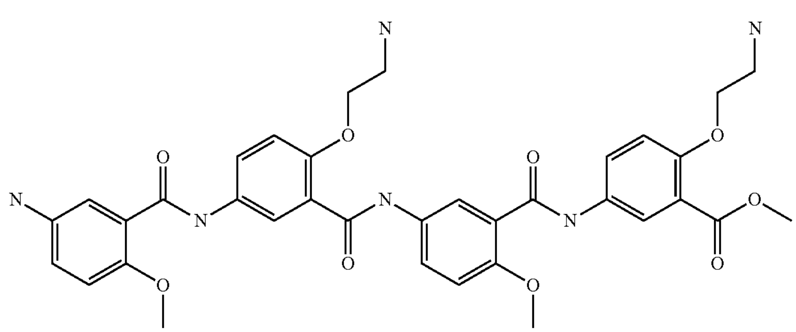 [SMILES: COC(=O)c1cc(NC(=O)c2cc(NC(=O)c3cc(NC(=O)c4cc(N)ccc4OC)ccc3OCCN)ccc2OC)ccc1OCCN] |

TABLE 1-continued

Polycationic Compounds.

| Compound | Structure |
|---|---|
| Compound 53 | 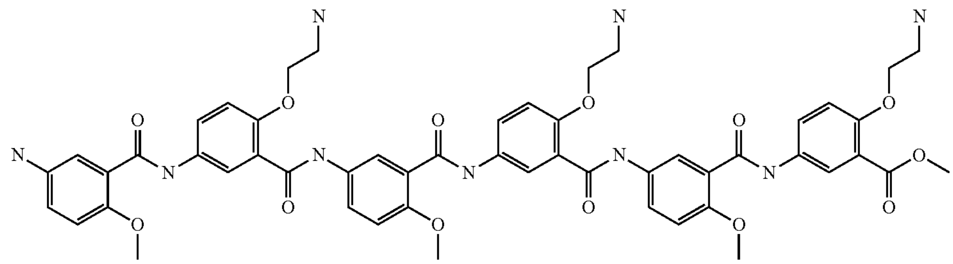 [SMILES: COC(=O)c1cc(NC(=O)c2cc(NC(=O)c3cc(NC(=O)c4cc(NC(=O)c5cc(NC(=O)c6cc(N)ccc6OC)ccc5OCCN)ccc4OC)ccc3OCCN)ccc2OC)ccc1OCCN] |
| Compound 54 | 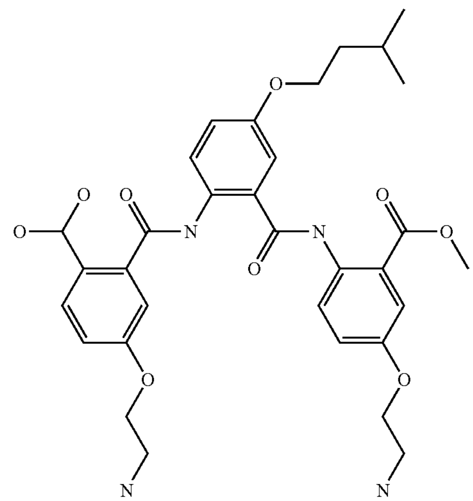 [SMILES: COC(=O)c1cc(OCCN)ccc1NC(=O)c1cc(OCCC(C)C)ccc1NC(=O)c1cc(OCCN)ccc1C(O)O] |
| Compound 55 | 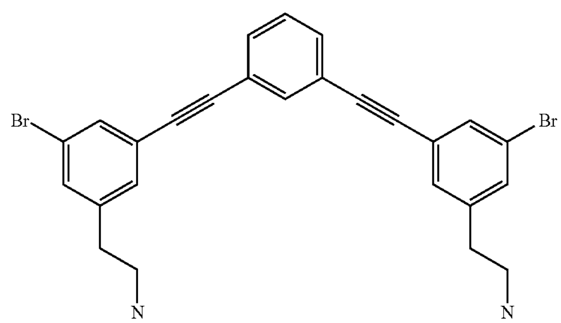 [SMILES: NCCc1cc(Br)cc(C#Cc2cccc(C#Cc3cc(Br)cc(CCN)c3)c2)c1] |

In more preferred embodiments, the polycationic compound comprises Compound 26, Compound 28, Compound 29, Compound 34, Compound 48, or Compound 50 or a combination thereof.

Other polycationic compounds useful in the methods of the present invention are those described in WO 02/072007 entitled "Facially Amphiphilic Polymers as Anti-Infective Agents" filed Mar. 7, 2002, WO 02/100295 entitled "Facially Amphiphilic Polymers as Anti-Infective Agents" filed Mar. 7, 2002 and WO 04//082634 entitled "Facially Amphiphillic Polymers and Oligomers and Uses Thereof" filed on Mar. 17, 2004.

In another embodiment, a compound is provided for modulating angiogenesis comprising a therapeutically effective amount of a polycationic compound.

In one embodiment of the invention, the polycationic compound is an arylamide oligomer compound of the formula:

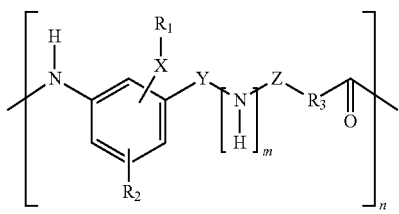

wherein
X is O or S;
R₁ is C₁-C₉ straight or branched chain alkyl,
wherein R₁ is optionally substituted with one or more —NH₂ or

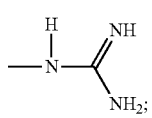

Y is a bond or

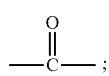

Z is a bond or

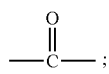

R₂ is hydrogen or C₁-C₉ straight or branched chain alkyl;
wherein said R₂ is optionally substituted with one or more —NH₂ or

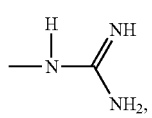

or R₂ is —X—R₁;
R₃ is

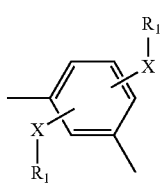

or methylene,
wherein said methylene is substituted with C₁ to C₉ straight or branched chain alkyl, wherein said C₁ to C₉ straight or branched chain alkyl is optionally substituted with one or more —NH₂ or

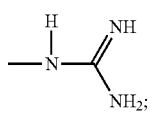

n is 2-10; and
m is 1 or 2.

In a preferred embodiment, the compound is an arylamide of the formula:

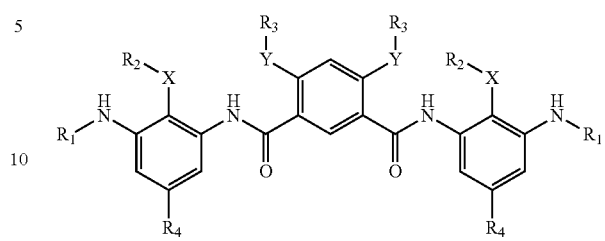

X is O or S;
Y is O or S;
R₁ is H or —C(=O)-A, A is C₁ to C₉ straight or branched alkyl, where A is optionally substituted with one or more —NH₂, —N(CH₃)₂ or

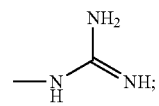

R₂ is C₁ to C₉ straight or branched alkyl, where R₂ is optionally substituted with one or more —NH₂, —N(CH₃)₂ or

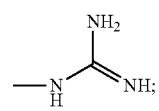

R₃ is C₁ to C₉ straight or branched alkyl, where R₃ is optionally substituted with one or more —NH₂, —N(CH₃)₂ or

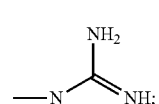

R₄ is H, —B or —C(=O)—O—B, where B is C₁ to C₉ straight or branched alkyl.

In another embodiment, the polycationic compound is a hydrazide of the formula:

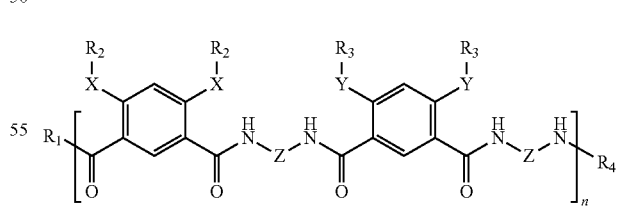

n=1 to 10;
X is O or S;
Y is O or S;
Z is a bond, C₁ to C₉ straight or branched alkyl, or a 1,4-cyclohexyl
R₁ is NH₂ or NH-A, where A is C₁ to C₉ straight or branched alkyl, where A is optionally substituted with —NH₂, —N(CH₃)₂ or

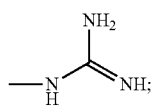

$R_2$ is $C_1$ to $C_9$ straight or branched alkyl, where $R_2$ is optionally substituted with one or more —$NH_2$, —$N(CH_3)_2$ or

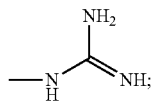

$R_3$ is $C_1$ to $C_9$ straight or branched alkyl, where $R_3$ is optionally substituted with one or more —$NH_2$, —$N(CH_3)_2$ or

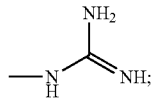

$R_4$ is H or

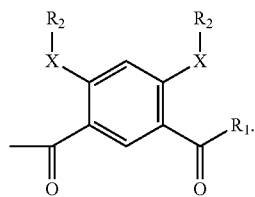

In another embodiment, the polycationic compound is a calixrene of the formula:

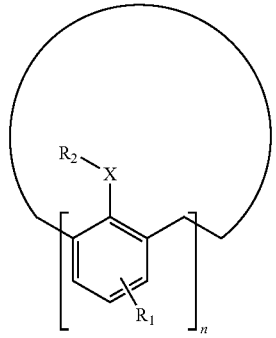

n=2-8, more preferably 4-8;
X is a bond, O or —O—$CH_2$—C(=O)—O—,
$R_1$ is -A or —O-A, where A is $C_1$ to $C_9$ straight or branched alkyl;
$R_2$ is $C_1$ to $C_9$ straight or branched alkyl, where $R_2$ is optionally substituted with one or more —$NH_2$, —$N(CH_3)_2$ or

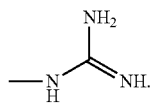

In another embodiment of the invention, the polycationic compound is a salicylamide of the formula:

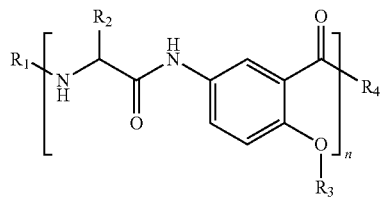

n is 2 to 10;
$R_1$ is H or

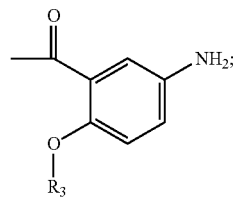

$R_2$ is $C_1$ to $C_9$ straight or branched alkyl, where $R_2$ is optionally substituted with one or more —$NH_2$, —$N(CH_3)_2$ or

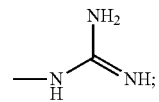

$R_2$ is $C_1$ to $C_9$ straight or branched alkyl, where $R_2$ is optionally substituted with one or more —$NH_2$, —$N(CH_3)_2$ or

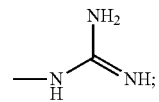

$R_4$ is OH, $NH_2$ or

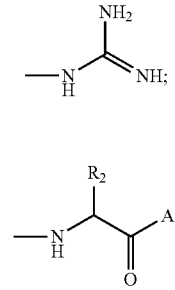

where A is OH or $NH_2$.

In preferred embodiments, the compound comprises Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, Compound 27, Compound 28, Compound 29, Compound 30, Compound 31, Compound 32, Compound 33, Compound 34, Compound 35, Compound 26, Compound 37, Compound 38, Compound 39, Compound 40, Compound 41, Compound 42, Compound 43, Compound 44, Compound 45, Compound 46, Compound 47, Compound 48, Compound 49, Compound 50, Compound 51, Compound 52, Compound 53, Compound 54, Compound 55, or a combination thereof.

In more preferred embodiments, the compound comprises Compound 26, Compound 28, Compound 29, Compound 34, Compound 48, or Compound 50 or a combination thereof.

Salicylamide polycationic compounds may be synthesized as follows:
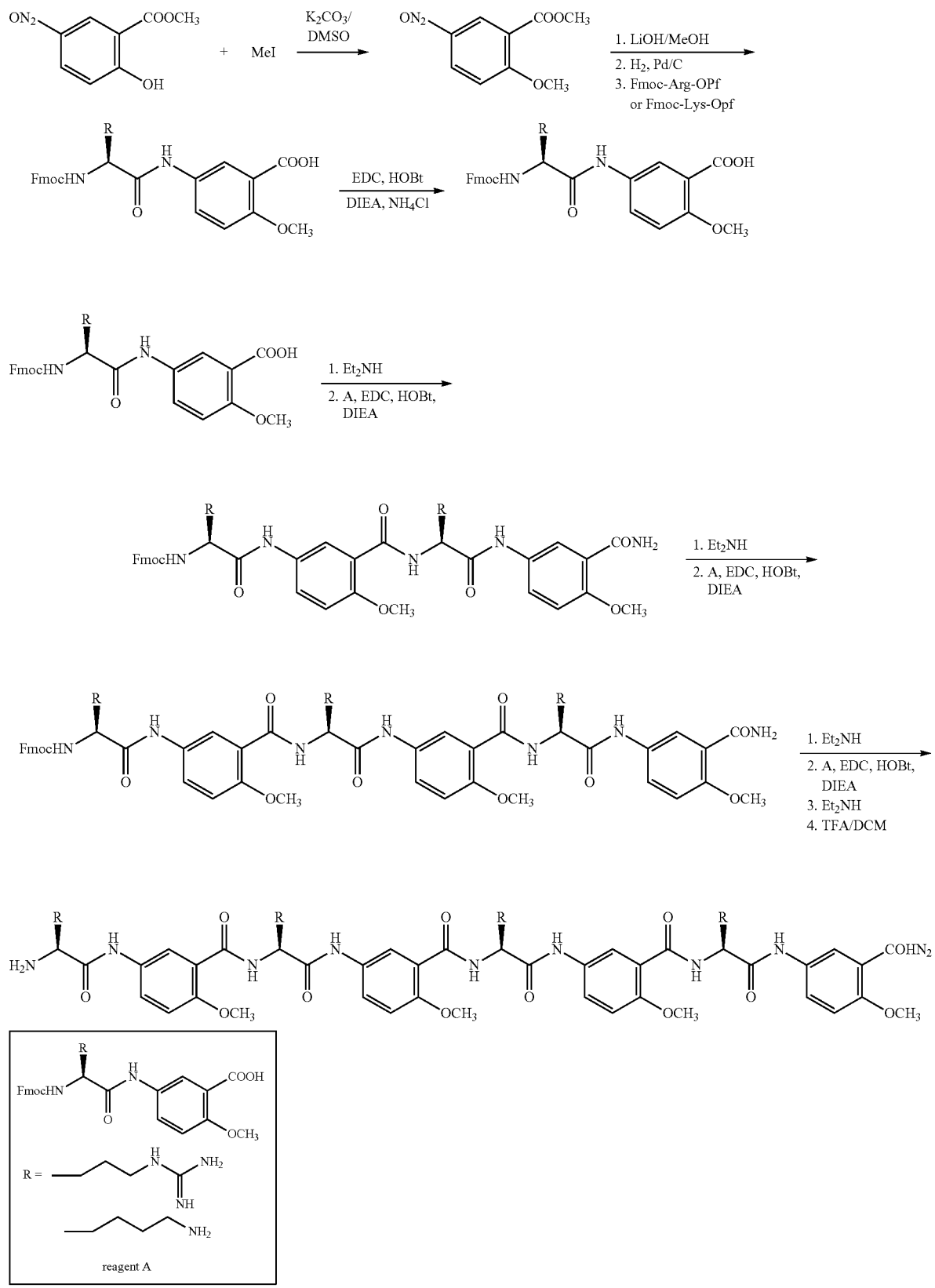

In another embodiment, a compound is provided for modulating angiogenesis comprising a therapeutically effective amount of a polycationic compound.

In one embodiment, the compound may contain a therapeutically effective amount of a polycationic compound to promote angiogenesis. In a preferred embodiment, the compound may contain a therapeutically effective amount of a polycationic compound to inhibit angiogenesis.

In a preferred embodiment, the compound is an arylamide of the formula:

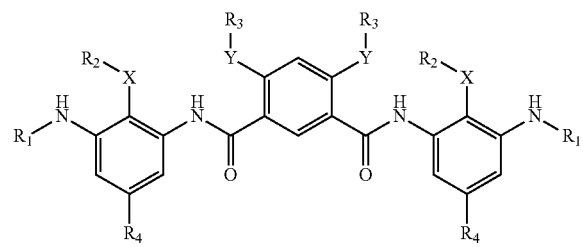

X is O or S;
Y is O or S;
$R_1$ is H or —C(=O)-A, A is $C_1$ to $C_9$ straight or branched alkyl, where A is optionally substituted with one or more —$NH_2$, —$N(CH_3)_2$ or

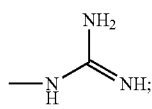

$R_2$ is $C_1$ to $C_9$ straight or branched alkyl, where $R_2$ is optionally substituted with one or more —$NH_2$, —$N(CH_3)_2$ or

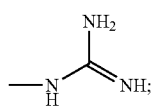

$R_3$ is $C_1$ to $C_9$ straight or branched alkyl, where $R_3$ is optionally substituted with one or more —$NH_2$, —$N(CH_3)_2$ or

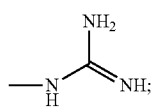

$R_4$ is H, —B or —C(↑O)—O—B, where B is $C_1$ to $C_9$ straight or branched alkyl.

In another embodiment, the polycationic compound is a hydrazide of the formula:

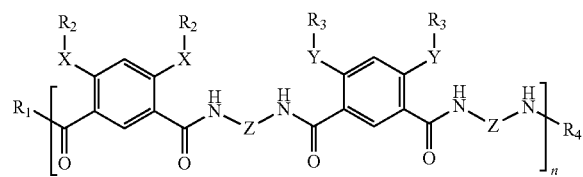

n=1 to 10;
X is O or S;
Y is O or S;
Z is a bond, $C_1$ to $C_9$ straight or branched alkyl, or a 1,4-cyclohexyl
$R_1$ is $NH_2$, or NH-A, where A is $C_1$ to $C_9$ straight or branched alkyl, where A is optionally substituted with —$NH_2$, —$N(CH_3)_2$ or

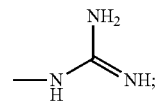

$R_2$ is $C_1$ to $C_9$ straight or branched alkyl, where $R_2$ is optionally substituted with one or more —$NH_2$, —$N(CH_3)_2$ or

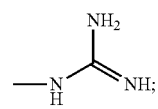

$R_3$ is $C_1$ to $C_9$ straight or branched alkyl, where $R_3$ is optionally substituted with one or more —$NH_2$, —$N(CH_3)_2$ or

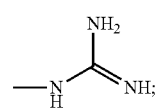

$R_4$ is H or

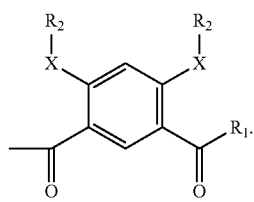

In another embodiment of the invention, the polycationic compound is a calixarene of the formula:

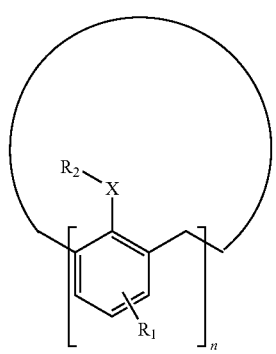

n=2-8, more preferably 4-8;
X is a bond, O or —O—$CH_2$—C(=O)—O—,
$R_2$ is -A or —O-A, where A is $C_1$ to $C_9$ straight or branched alkyl;

$R_2$ is $C_1$ to $C_9$ straight or branched alkyl, where $R_2$ is optionally substituted with one or more —$NH_2$, —$N(CH_3)_2$ or

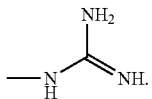

In another embodiment of the invention, the polycationic compound is a salicylamide of the formula:

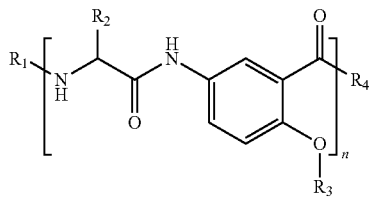

n is 2 to 10;
$R_1$ is H or

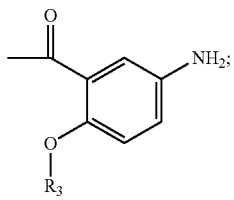

$R_2$ is $C_1$ to $C_9$ straight or branched alkyl, where $R_2$ is optionally substituted with one or more —$NH_2$, —$N(CH_3)_2$ or

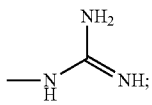

$R_3$ is $C_1$ to $C_9$ straight or branched alkyl, where $R_2$ is optionally substituted with one or more —$NH_2$, —$N(CH_3)_2$ or

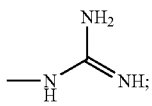

$R_4$ is OH, $NH_2$, or

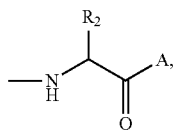

where A is OH or $NH_2$.

In one aspect of the present invention, the polycationic compounds of the present invention may be useful in the treatment of a disease or disorder associated with angiogenesis. In preferred embodiments, the compound comprises a therapeutically effective amount of Compound 26, Compound 28, Compound 29, Compound 34, Compound 48, or Compound 50 or a combination thereof.

In another embodiment of the invention, the polycationic compounds may be used to treat or prevent a disease or disorder associated with insufficient angiogenesis. Such diseases include, for example, stroke, heart disease, ulcers, infertility and scleroderma.

In one embodiment of the invention, the polycationic compounds may be used to treat or prevent a disease or disorder associated with excessive angiogenesis. Such diseases include, for example, cancer, rheumatoid arthritis, AIDS complications, psoriasis and blindness.

Generally, cancer refers to any malignant growth or tumor caused by abnormal and uncontrolled cell division; it may spread to other parts of the body through the lymphatic system or the blood stream. Cancer include both solid tumors and blood-borne tumors. Solid tumors include, or example, but not limited to Kaposi's sarcoma, hemangiomas, solid tumors, blood-borne tumors, breast cancer, lung cancer, ovarian cancer, testicular cancer, colon cancer, rhabdomyosarcoma, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia-like tumors.

In yet another embodiment of the invention, the disease or disorder is lung cancer, breast cancer, prostate cancer, colon cancer, renal cancer, bladder cancer, pancreatic cancer, glioblastoma, neuroblastoma, blindness, macular degeneration, diabetic retinopathy, corneal transplant, myopic degeneration, complications related to AIDS, arthritis, rheumatoid arthritis, psoriasis, scleroderma, inflammatory bowel disease, stroke, heart disease, ulcers and infertility. For example, but not limited to, cancers, inflammatory arthritis (such as rheumatoid arthritis), diabetic retinopathy, as well as other neovascular diseases of the eye (or example, corneal neovascularization, neovascular glaucoma, retrolental fibroblasia and macular degeneration), arteriovenous malformations, conditions of excessive bleeding (menorrhagia), Osler-Weber Syndrome, myocardial angiogenesis, plaque neovascularization, telangiectasia, hemophiliac joints, angiofibroma, and wound granulation. The anti-angiogenic compositions provided herein are also useful in the treatment of diseases of excessive or abnormal stimulation of endothelial cells. These diseases include, but are not limited to, intestinal adhesions, Crohn's disease, atherosclerosis, scleroderma, and hypertrophic scars (i.e., keloids).

Other suitable angiogenesis-mediated disorders that may be treated or prevented with the polycationic compounds provided include, but are not limited to, tumors and cancer associated disorders (e.g., retinal tumor growth, benign tumors (e.g., hemangiomas, acoustic neuromas, neurofibromas, trachomas, and pyogenic granulomas), solid tumors, blood borne tumors (e.g., leukemias, angiofibromas, and kaposi sarcoma), tumor metastases, and other cancers which require neovascularization to support tumor growth), ocular neovascular-disorders (e.g., diabetic retinopathy, macular degeneration, retinopathy of prematurity, neovascular glaucoma, corneal graft rejection, and other ocular angiogenesis-mediated disorders), inflammatory disorders (e.g., immune and non-immune inflammation, rheumatoid arthritis, chronic articular rheumatism, inflammatory bowel diseases, psoriasis, and other chronic inflammatory disorders), endometriosis, other disorders associated with inappropriate or inopportune invasion of vessels (e.g., retrolental fibroplasia, rubeosis, and capillary proliferation in atherosclerotic plaques and osteoporosis), Osler-Webber Syndrome, myocardial angiogenesis, plaque neovascularization, telangiectasia, hemophiliac joints, and wound granulation. Other diseases in which angiogenesis plays a role in the maintenance or progression of the pathological state are known to those skilled in the art and are similarly intended to be included within the meaning of the term angiogenesis-mediated used herein.

In one embodiment, the polycationic compounds are used in conjunction with other angiogenesis inhibitors. Angiogenic inhibitors are known in the art and can be prepared by known methods. For a description of angiogenic inhibitors and targets sec, for example, Chen et al., Cancer Res. 55:4230-4233 (1995), Good et al., Proc. Natl. Acad. Sci. USA 87:6629-6628 (1990), O'Reilly et al., Cell 79:315-328 (1994), Parangi et al., Proc. Natl. Acad. Sci. USA 93:2002-2007 (1996), Rastinejad et al., Cell 56:345-355 (1989), Gupta et al., Proc. Natl. Acad. Sci. USA 92:7799-7803 (1995), Maione et al., Science 247:77-79 (1990), Angiolillo et al., J. Exp. Med. 182:155-162 (1995), Strieter et al., Biochem. Biophys. Res. Comm. 210:51-57 (1995); Voest et al., J. Natl. Cancer Inst. 87:581-586 (1995), Cao et al., J. Exp. Med. 182:2069-2077 (1995), and Clapp et al., Endocrinology 133: 1292-1299 (1993), which are hereby incorporated by reference in their entirety. For a description of additional angiogenic inhibitors see, for example. Blood et al., Bioch. Biophys Acta., 1032:89-118 (1990), Moses et al., Science, 248:1408-1410 (1990), Ingber et al., Lat Invest., 59:44-51 (1988), and U.S. Pat. Nos. 5,092,885 and 5,112,946, which are hereby incorporated by reference in their entirety.

In another embodiment, the polycationic compounds are used in conjunction with other therapies, such as standard anti-inflammatory therapies, standard ocular therapies, standard dermal therapies, radiotherapy, tumor surgery, and conventional chemotherapy directed against solid tumors and for the control of establishment of metastases. The administration of the angiogenesis inhibitor is typically conducted during or after chemotherapy at time where the tumor tissue should respond to toxic assault by inducing angiogenesis to recover by the provision of a blood supply and nutrients to the tumor tissue. Additionally, it is preferred to administer such angiogenesis inhibitors after surgery where solid tumors have been removed as a prophylaxis against metastasis. Cytotoxic or chemotherapeutic agents are those known in the art such as aziridine thiotepa, alkyl sulfonate, nitrosoureas, platinum complexes, NO classic alkylators, folate analogs, purine analogs, adenosine analogs, pyrimidine analogs, substituted urea, antitumor antibiotics, microtubulle agents, and asprignase.

Another aspect of this invention relates to the use of polycationic compounds in the inhibition of angiogenesis-mediated processes alone or in combination with other existing anti-inflammatory, anti-angiogenesis, anti-cancer, and ocular therapies. Polycationic compounds represent an effective strategy for the prevention and treatment of angiogenesis-mediated disorders in cancer, inflammatory, and ocular diseases.

The compounds described above may be administered in a formulation including polycationic compounds and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound of formula (I), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Micro-spheres or nano-spheres formed of polymers or proteins are well known to those skilled in the art, and can be tailored for passage through the gastrointestinal tract directly into the blood stream. Alternatively, the compound can be incorporated and the micro-spheres/nano-spheres, or composite of both, implanted for slow release over a period of time ranging from days to months. See, for example, U.S. Pat. Nos. 4,906,474, 4,925,673 and 3,625,214, and Jein, TIPS19: 155-157 (1998), the contents of which are hereby incorporated by reference.

The polycationic compounds of the present invention exhibit anti-angiogenic effects in vitro and in vivo. In addition, the polycationic compounds of the present invention exhibit antagonistic effects against heparin. While not wishing to be bound by theory, the anti-angiogenic effects of the polycationic compounds may be due, at least in part to the polycationic compounds ability to antagonize heparin's role in facilitating activation of FGF and VEGF receptors.

For the following examples, various materials were obtained as follows. All reagents were chemical grade and purchased from Sigma Chemical Co. (St. Louis, Mo.) or through VWR Scientific (Bridgeport, N.J.). Cortisone acetate, bovine serum albumin (BSA), and gelatin solution (2% type B from bovine skin) were purchased from Sigma Chemical Co. (St. Louis, Mo.). M199 growth medium with Earl's salts, basic FGF, Insulin-Transferrin-Selenium-G Supplement (1-T-Se) 100×, Dulbecco's phosphate buffered salt solution (PBS) with and without $Ca^{+2}$ and $Mg^{+2}$, and 0.5 M EDTA were obtained from Gibco BRL (Grand Island, N.Y.). Human umbilical vein endothelial cells (HUVEC), endothelial cell basal medium (serum-free, EBM), endothelial growth medium (EGM) (supplemented with growth factors, fetal calf serum), and 0.025% trypsin/0.01% EDTA solution were purchased from Clonetics Inc. (San Diego, Calif.). Human prostrate (TSU-Pr) tumor cells were obtained from American Type Culture Collection (Rockville, Md.). Matrigel® matrix and human collagen type III were purchased from Becton Dickinson (Bedford, Mass.). HEMA-3 fixative and staining solutions were purchased from Biochemical Sciences, Inc. (Swedesboro, N.J.). Fertilized chicken eggs were purchased from Charles River Laboratories, SPAFAS Avian Products & Services (North Franklin, Conn.). In vivo neovascularization was examined by the method previously described by Auerbach et al. (Auerbach et al., J. Dev. Biol., 41:391-394 (1974), which is hereby incorporated by reference in its entirety).

Example 1

The following example illustrates the anti-angiogenic effect of exemplary polycationic compounds of the present invention. Ten-day old embryos were purchased from Spafas, Inc. (Preston, Conn.) and were incubated at 37° C. with 55% relative humidity. In the dark with the help of a candling lamp, a small hole was punctured in the shell concealing the air sac with a hypodermic needle. A second hole was punctured in the shell on the broadside of the egg directly over an avascular portion of the embryonic membrane, as observed during candling. A false air sac was created beneath the second hole by the application of negative pressure to the first hole, which caused the chorioallantoic membrane (CAM) to separate from the shell. A window, approximately 1.0 $cm^2$, was cut in the shell over the dropped CAM with the use of a small crafts grinding wheel (Dremel, Division of Emerson Electric Company Racine, Wis.) which allowed direct access to the underlying CAM. Filter disks of #1 filter paper (Whatman International, United Kingdom) were soaked in 3 mg/mL cortisone acetate (Sigma, St. Louis, Mo.) in a solution of 95% ethanol and water and subsequently air dried under sterile conditions. FGF2 (Life Technologies, Gaithersburg, Md.) was used to grow vessels on the CAMs of 10 day old chick embryos. Sterile filter disks adsorbed with FGF2 dissolved in PBS at 1 µg/mL were placed on growing CAMs. Sterile filter disks adsorbed with FGF2 was dissolved in PBS at 1 µg/mL were placed on growing CAM. At 24 h, test compounds or control vehicle was added directly to CAM topically.

CAM tissue directly beneath FGF2-saturated filter disk was resected from embryos treated 48 hours prior with test compound or control. Tissues were washed three times with PBS. Sections were placed in a 35-mm petri dish (Nalgen Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed using Image-Pro Plus software (Media Cybernetics, Silver Spring, Md.). Table 4 contains the number of vessel branch points contained in a circular region equal to the area of a filter disk counted for each section.

CAM tissue directly beneath FGF2-saturated filter disk was resected from embryos treated 48 h prior with compound or control. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed with the Image-Pro Plus software (Media Cybernetics, Silver Spring, Md.). The effects of polycationic compounds on angiogenesis are shown in Tables 2, 3 and 4. The effects are also shown in FIG. 1.

TABLE 2

Anti-angiogenesis efficacy of polycationic compounds in CAM model

| CAM Treatment | Branch pts ± SEM | % Inhibition ± SEM |
|---|---|---|
| PBS (control) | 69 ± 16.0 | |
| FgF (1.0 ug/ml) | 155 ± 10 | |
| Compound 29 (1.2 ug) + FGF2 (1 ug) | 82 ± 5 | 85 ± 6 |

Data represents mean + SEM, n = 8

TABLE 3

Anti-angiogenesis efficacy of polycationic compound in CAM model

| CAM Treatment | Branch pts ± SEM | % inhibition ± SEM |
|---|---|---|
| PBS (control) | 80 ± 7 | |
| FgF2 (1.0 ug/ml) | 177 ± 10 | |
| Compound 26 (1.0 ug) + FGF2(1 ug) | 123 ± 7 | 55 ± 8 |
| Compound 34 (1.0 ug) + FGF2(1 ug) | 156 ± 9 | 21 ± 9 |
| Compound 40 (0.1 ug) + FGF2(1 ug) | 142 ± 6 | 36 ± 6 |
| Compound 36 (1.0 ug) + FGF2(1 ug) | 156 ± 6 | 21 ± 6 |
| Compound 33 (1.0 ug) + FGF2(1 ug) | 160 ± 18 | 17 ± 18 |
| Ccompound 27 (0.1 ug) + FGF2(1 ug) | 144 ± 9 | 34 ± 9 |

TABLE 4

Anti-angiogenesis efficacy of polycationic compound in CAM model

| Treatment Groups | Mean % inhibition ± SEM |
|---|---|
| PBS (Control | |
| FGF2 (1.0 ug/ml) | |
| Compound 50 (1.0 ug) + FGF2 (1 ug) | 21 ± 9 |
| Compound 50 (3.0 ug) + FGF2 (1 ug) | 42 ± 8 |
| Compound 50 (10 ug) + FGF2 (1 ug) | 66 ± 7 |
| Compound 48 (1.0 ug) + FGF2 (1 ug) | 16 ± 6 |
| Compound 48 (3.0 ug) + FGF2 (1 ug) | 38 ± 8 |
| Compound 48 (10 ug) + FGF2 (1 ug) | 55 ± 7 |

Data represent mean ± SEM, n = 8

As depicted in Tables 2, 3 and 4 above, the polycationic compounds blocked FGF2-induced angiogenesis in the CAM model of angiogenesis.

Example 2

The following example illustrates inhibition of endothelial cell tube formation by polycationic compounds of the present invention. Differentiation by endothelial cells was examined using a method developed by Grant et al. (Grant et al., *In Vitro Cell Dev. Biol.*, 27A:327-336 (1991). Matrigel® matrix, phenol-red free (commercially available from Becton Dickinson, Bedford, Mass.) was thawed overnight at 4° C. Using cold pipette tips, 3.0 mg/well of Matrigel® matrix was placed in a cold twenty-four-multiwell plate. Matrigel® matrix was allowed to polymerize during incubation at 37° C. for 30 minutes.

Human umbilical vein endothelial cells (HUVEC) were maintained at 37° C. with 5% $CO_2$ and 95% humidity in endothelial cell growth medium with 2% fetal bovine serum (EGM). The tube assay was performed in endothelial cell basal medium (EBM) supplemented with 0.5% bovine serum albumin (BSA) and 1:100 diluted Insulin-Transferrin-Selenium-G supplement (I-T-Se, 100×). HUVEC were trypsinized and centrifuged and, subsequently, washed twice in phosphate buffered saline (PBS). After counting, cell density was adjusted to 35,000 cells/mL.

A final concentration of 35,000 cells/mL/well was treated with recombinant human fibroblast growth factor basic (FGF2) at 100 ng/ml and polycationic compounds (see Table 1B) dissolved in EBM medium. Treated cells were incubated overnight at 37° C. with 5% $CO_2$ and 95% humidity to allow cell attachment.

Subsequently, the medium was aspirated and cells were fixed and stained using a modified HEMA-3 stain kit. Digital images of micro-titer well sections were collected using a DKC5000 3-CCD color video camera system (Toshiba America, New York, N.Y.) and analyzed using Image-Pro Plus software (Media Cybernetics, Silver Spring, Md.). The area and major axis length of stained cells having a tubular morphology was measured on the Matrigel® matrix surface (Becton Dickinson, Bedford, Pa.) counted from 5 images/well.

As illustrated in Table 5 below, polycationic compounds are potent inhibitors of EC tube formation in vitro.

TABLE 5

Anti-angiogenesis efficacy of polycationic compound in the human endothelial tube formation assay

| Treatment Groups | Mean % Inhibition ± SEM |
|---|---|
| Compound 29 (0.01 ug) | 25 ± 7 |
| Compound 29 (0.1 ug) | 42 ± 5 |
| Compound 29 (1.0 ug) | 76 ± 6 |

Data represent mean ± SEM, n = 3

Example 3

This example relates to cellular migration assays. These assays were performed using a Neuroprobe 96 well disposable chemotaxis chamber with an 8 μm pore size. This chamber allowed for quantitation of cellular migration towards a gradient of either vitronectin or osteopontin. Cultured cells were removed following a standardized method using EDTA/Trypsin (0.01%/0.025%). Following removal, the cells were washed twice and resuspended ($2\times10^6$/ml) in EBM (Endothelial cell basal media, Clonetics Inc.). Add either vitronectin or osteopontin (33 μl) at 0.0125-100 μg/ml to the lower wells of a disposable chemotaxis chamber, and then assemble using the preframed filter. The cell suspension (45 μl) was added to a polypropylene plate containing 5 μl of test agent at different concentrations and incubated for 10 minutes at 22° C. Add 25 μl of cell/test agent suspension to the upper filter wells then incubate overnight (22 hours at 37° C.) in a humidified cell culture incubator. After the overnight incubation, non-migrated cells and excess media were gently removed using a 12 channel pipette and a cell scraper. The filters were then washed twice in PBS (no $Ca^{+2}$ or $Mg^{+2}$) and fixed with 1% formaldehyde. Membranes of migrated cells were permeated with Triton X-100 (0.2%) then washed 2-3 times with PBS. The actin filaments of migrated cells were stained with rhodamine phalloidin (12.8 IU/ml for 30 minutes (22° C.). Rhodamine phalloidin was made fresh weekly and reused for up to 3 days, when stored protected from light at 4° C. Chemotaxis was quantitatively determined by fluorescence detection using a Cytofluor II (530 excitation/590 emission). All cell treatment and subsequent washings were carried out using a uniquely designed treatment/wash station. This station consisted of six individual reagent units each with a 30 ml volume capacity. Individual units were filled with one of the following reagents: PBS, formaldehyde, Triton X-100, or rhodamine-phalloidin. Using this technique, filters were gently dipped into the appropriate solution, thus minimizing migrated cell loss. This technique allowed for maximum quantitation of cell migration and provided reproducible results with minimal inter and intra assay variability (Bozarth et al, *Methods In Cell Science*, 19 (3): 179-187, 1997; Penno et al, *J. Method In Cell Science*, 19 (3): 189-195, 1997).

As illustrated in Table 6 below, the polycationic compounds of the present invention inhibit human umbilical vein endothelial migration.

TABLE 6

Effect of polycationic compound on human endothelial cell migration assay

| Treatment Groups | Mean % Inhibition ± SEM |
|---|---|
| Compound 29 (0.01 uM) | 19 ± 2 |
| Compound 29 (0.1 uM) | 40 ± 3 |
| Compound 29 (1.0 uM) | 67 ± 5 |

Data represent mean ± SEM, n = 3

Example 4

The following example illustrates the heparin antagonistic effects of polycationic compounds of the present invention. To determine the anti-heparin activity of the polycationic compounds an assay measuring the percent inhibition using a fixed concentration of polycationic compound or concentrations of polycationic compounds causing lysis of 50% of human red blood cells were conducted.

10 IU of anti-thrombin was dissolved in 10 ml of buffer, resulting in a 1 IU/ml stock solution (250×) of the anti-thrombin. The 1 IU/ml (250×) stock solution of anti-thrombin and a 336 mM stock solution of NaCl were diluted into a total volume of 50 µl buffer so that the final anti-thrombin concentration was 0.004 IU/sample well and the NaCl was 150 mM/sample well. 1 µl of the compound to be tested, final concentration 10 µg/ml (corresponding to 0.5 logarithmic antagonist dilution) is added to the sample well. The samples are mixed and allowed to incubate at room temperature for 20 minutes. 50 µl of factor Xa dissolved in buffer is added to the sample well to a final concentration of 0.14 knat/well (2 IA of the 7.1 knat/ml stock solution to a final sample well buffer volume of 100 µl). The samples were mixed and further incubated at room temperature for 10 minutes. 10 µl of a 4 mM stock solution of the substrate S-2765 was added to each sample well for a final concentration of 0.4 mM in each sample well. The samples were mixed and hydrolyses of the chromogenic substrate Z-D-Arg-Gly-Arg-pNA (S-2765), thus liberating the chromophoric group pNA (p-nitroaniline), was monitored at 405 nm. The samples were mixed every 30 seconds to maintain a uniform mixture. ThermoLabsystems Multiskan Spectrum spectrophotometer was used to measure the absorbance spectrums. The increase in absorbance was proportional to the enzyme (factor Xa) activity. The % inhibition of factor Xa was determined using a standard curve. Results are depicted in Table 7. A bar graph also illustrating the percent inhibition is presented in FIG. 2.

TABLE 7

% FactorXa Inhibition: Single concentration (10 ug/ml)

| Compound # | % Inhibition | Compound # | % Inhibition |
|---|---|---|---|
| 9 | 16.24689847 | 25 | 0 |
| 10 | 20.80146834 | 26 | 48.14324 |
| 11 | 1.903402332 | 27 | 8.885942 |
| 12 | 9.381054349 | 28 | 44.29708 |
| 13 | 36.84443085 | 30 | 49.96431121 |
| 24 | 1.835423677 | 31 | 75.45630672 |
| 5 | 39.767513 | 32 | 23.1127426 |
| 19 | 59.82121614 | 33 | 32.01794636 |
| 15 | 5.710206995 | 34 | 99.99660107 |
| 14 | 40.99112879 | 37 | 62.40440502 |
| 17 | 15.02328269 | 35 | 79.60300466 |
| 18 | 13.25583767 | 38 | 65.05557255 |
| 1 | 22.29699874 | 39 | 56.49026206 |
| 2 | 41.05910744 | 41 | 7.817545291 |
| 4 | 0.951701166 | 46 | 59.14142959 |
| 3 | 2.855103498 | 42 | 79.46704735 |
| 6 | 2.583188879 | 43 | 59.68525883 |
| 7 | 5.506271031 | 45 | 77.83555963 |
| 8 | 7.409673363 | 44 | 74.36864824 |
| 9 | 10.87658475 | 52 | 45.47772 |
| 20 | 7.851534618 | 53 | 43.03048843 |
| 21 | 1.495530403 | 54 | 19.98572448 |
| 22 | 1.291594439 | 55 | 46.49739982 |
| 23 | 1.223615785 | Magainin | 4.418612556 |
| 16 | 30.38645865 | Magainin-T | 23.1127426 |

Figure 2:
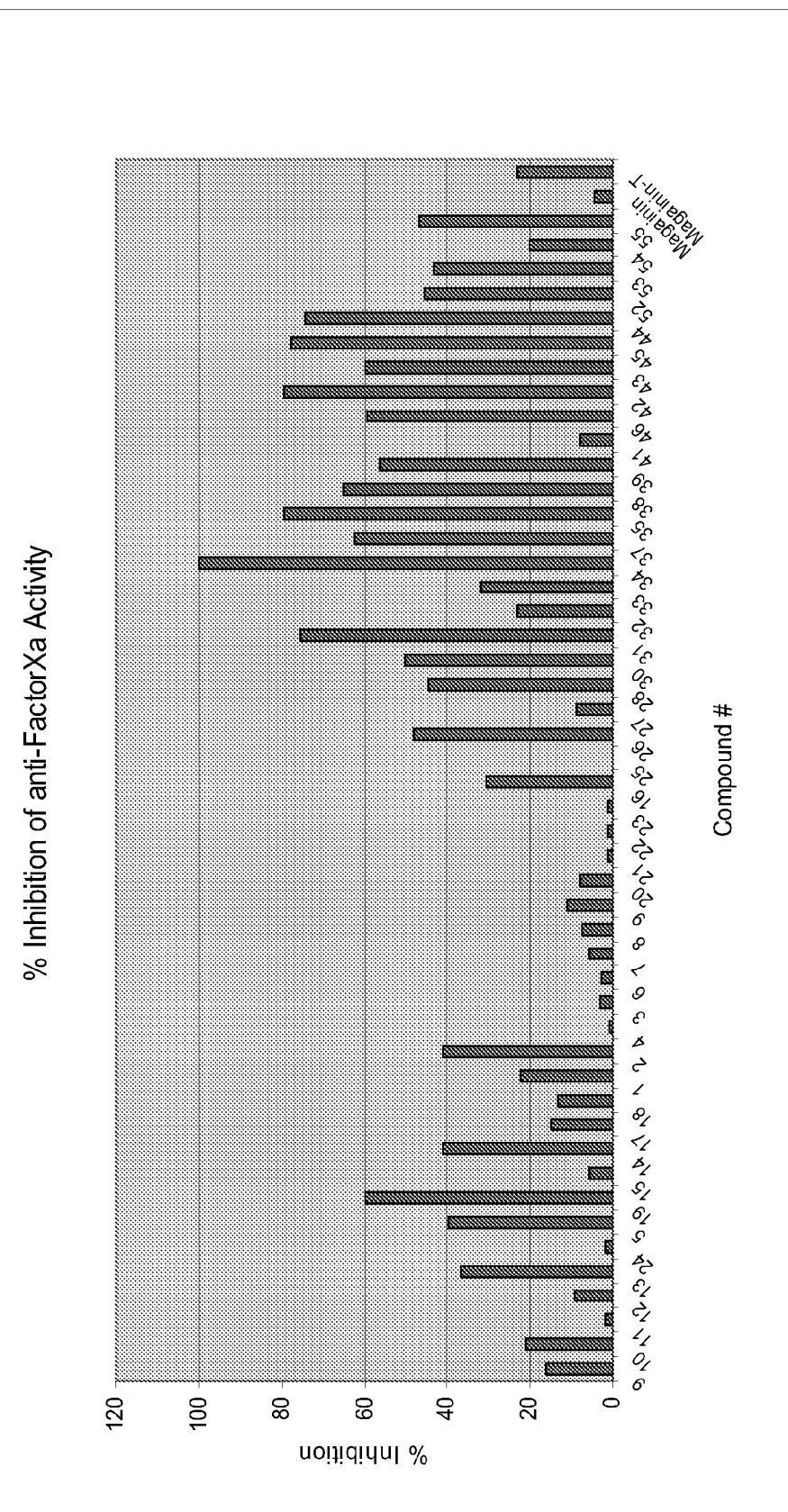
FIG. 2 is a bar graph depicting the percent inhibition of Factor Xa of polycationic compounds of the present invention.

As illustrated in FIG. 2 and Table 7 above, the polycationic compounds of the present invention inhibited Factor Xa.

Factor Xa Inhibition: EC50. To determine the concentration of polycationic compound that causes about 50% lysis of human red blood cells, fixed heparin concentrations were used and different amounts of heparin antagonists were added. Results are depicted in Table 8.

TABLE 8

FactorXa Inhibition: EC50

| Compound | MW | $EC_{50}$ (µM) | $HC_{50}$ (µg/ml) | $HC_{50}$ (µM) |
|---|---|---|---|---|
| Compound 27 | 783 | 9.7 | >2,000 | |
| Compound 25 | 615 | 5.3 | >2,000 | |
| Compound 26 | 927 | 2.0 | >2,000 | |
| Compound 7 | 921 | 3.7 | 715 | 519 |
| Compound 50 | 1126 | 0.36 | 637 | 377 |
| Compound 48 | 1238 | 0.077 | 261 | 144 |
| Compound 47 | 933 | 5.54 | | |
| Compound 51 | 1070 | 16.7 | | |
| Compound 49 | 849 | 22 | | |

As illustrated in Table 7 above, the polycationic compounds of the present invention exhibit varying degrees of inhibition of Factor Xa.

Example 5

Figure 3:
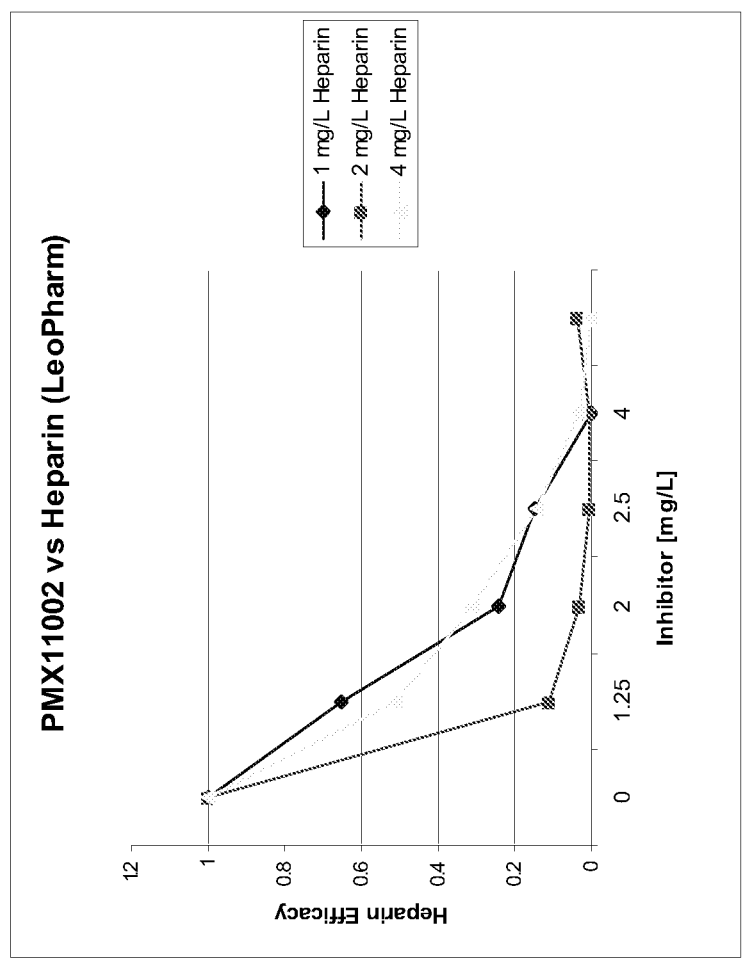
FIG. 3 is a graph depicting the effect of Compound 26, a polycationic compound of the present invention, on coagulation time.

The following example illustrates the effect of a polycationic compound of the present invention on coagulation time. The anti-heparin assay as described herein was used. The assay contained either 1 mg/L, 2 mg/L or 4 mg/l of heparin and increasing amounts of Compound 26 was added. Table 9 and FIG. 3 depict the effect of Compound 26 on coagulation time.

TABLE 9

Effect of Compound 26 on coagulation time and heparin efficacy

| Heparin (mg/L) | Compound 26 (mg/L) | Coagulation Time (s) | Heparin Efficacy |
|---|---|---|---|
| 1 | 0 | 50.8 | 1 |
| 1 | 1.25 | 42.8 | 0.65065 |
| 1 | 2 | 33.4 | 0.24017 |
| 1 | 2.5 | 31.3 | 0.14847 |
| 1 | 4 | 27.9 | −1.67E−08 |
| 2 | 0 | 110.8 | 1 |
| 2 | 2.5 | 40.2 | 0.11083 |
| 2 | 4 | 33.9 | 0.031486 |
| 2 | 5 | 31.9 | 0.0062972 |
| 2 | 6 | 31.8 | 0.0050378 |
| 2 | 10 | 34.4 | 0.037783 |
| 4 | 0 | 214.9 | 1 |
| 4 | 2.5 | 124.8 | 0.51297 |
| 4 | 4 | 87.4 | 0.31081 |
| 4 | 5 | 55.8 | 0.14 |
| 4 | 6 | 35.4 | 0.02973 |
|  | 10 | 29.9 | −2.06E−09 |

As illustrated in FIG. 3 and Table 9, above, Compound 26, a polycationic compound of the present invention decreased the coagulation time in varying concentrations of heparin, evidencing the compounds ability to antagonize heparin's activity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:
1. A compound of the formula:

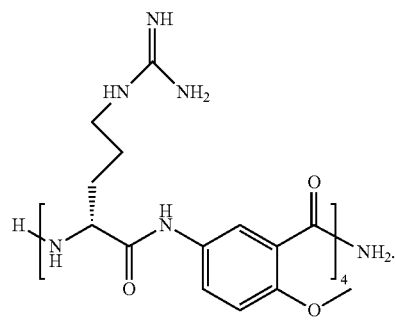

2. A composition comprising the compound of claim 1 and a pharmaceutically acceptable carrier.

3. The composition of claim 2 which is in the form of a capsule, cachet, tablet or lozenge.

4. The composition of claim 2 which is in the form of a powder or granule.

5. The composition of claim 2 which is in the form of a suspension or solution in an aqueous liquid or non-aqueous liquid.

6. A method of antagonizing heparin in a mammal comprising administering the compound of claim 1 to said mammal.

7. A method of antagonizing heparin in a mammal comprising administering the composition of claim 2 to said mammal.

8. A method of inhibiting anti-Factor Xa in a mammal comprising administering the compound of claim 1 to said mammal.

9. A method of inhibiting anti-Factor Xa in a mammal comprising administering the composition of claim 2 to said mammal.

10. The method of claim 6 wherein the mammal is a human.

11. The method of claim 7 wherein the mammal is a human.

12. The method of claim 8 wherein the mammal is a human.

13. The method of claim 9 wherein the mammal is a human.

* * * * *